(12) United States Patent
Sanders et al.

(10) Patent No.: US 8,703,416 B2
(45) Date of Patent: Apr. 22, 2014

(54) METHOD FOR PURIFICATION AND IDENTIFICATION OF SPERM CELLS

(75) Inventors: Glenn Sanders, Boulder, CO (US); Evaldas Katilius, Superior, CO (US); Larry Gold, Boulder, CO (US)

(73) Assignee: SomaLogic, Inc., Boulder, CO (US)

( * ) Notice: Subject to any disclaimer, the term of this patent is extended or adjusted under 35 U.S.C. 154(b) by 0 days.

(21) Appl. No.: 13/525,271

(22) Filed: Jun. 15, 2012

(65) Prior Publication Data

US 2012/0264117 A1 Oct. 18, 2012

Related U.S. Application Data

(63) Continuation-in-part of application No. 13/382,493, filed as application No. PCT/US2010/041540 on Jul. 9, 2010, which is a continuation-in-part of application No. 12/499,967, filed on Jul. 9, 2009, now Pat. No. 7,964,356, which is a continuation-in-part of application No. 12/175,434, filed on Jul. 17, 2008, now Pat. No. 7,947,447, application No. 13/525,271, which is a continuation-in-part of application No. 12/958,620, filed on Dec. 2, 2010, which is a continuation-in-part of application No. 12/175,446, filed on Jul. 17, 2008, now Pat. No. 7,855,054.

(60) Provisional application No. 60/950,283, filed on Jul. 17, 2007, provisional application No. 60/950,281, filed on Jul. 17, 2007, provisional application No. 60/950,293, filed on Jul. 17, 2007, provisional application No. 61/031,420, filed on Feb. 26, 2008, provisional application No. 61/051,594, filed on May 8, 2008, provisional application No. 61/498,224, filed on Jun. 17, 2011.

(51) Int. Cl.
*C12Q 1/68* (2006.01)
*C07H 21/00* (2006.01)

(52) U.S. Cl.
USPC .......................................... 435/6.1; 536/22.1

(58) Field of Classification Search
None
See application file for complete search history.

(56) References Cited

U.S. PATENT DOCUMENTS

| | | | |
|---|---|---|---|
| 4,562,157 A | 12/1985 | Lowe et al. |
| 4,737,453 A | 4/1988 | Primus et al. |
| 4,752,566 A | 6/1988 | Collins et al. |
| 5,124,246 A | 6/1992 | Urdea et al. |
| 5,270,163 A | 12/1993 | Gold et al. |
| 5,412,087 A | 5/1995 | McGall et al. |
| 5,475,096 A | 12/1995 | Gold et al. |
| 5,567,588 A | 10/1996 | Gold et al. |
| 5,580,737 A | 12/1996 | Polisky |
| 5,582,981 A | 12/1996 | Toole et al. |
| 5,599,720 A | 2/1997 | Ekins et al. |
| 5,614,503 A | 3/1997 | Chaudhary et al. |
| 5,639,868 A | 6/1997 | Janjic et al. |
| 5,658,738 A | 8/1997 | Nadeau et al. |
| 5,681,697 A | 10/1997 | Urdea et al. |
| 5,688,935 A | 11/1997 | Stephens et al. |
| 5,712,375 A | 1/1998 | Jensen et al. |
| 5,750,342 A | 5/1998 | Stephens et al. |
| 5,763,177 A | 6/1998 | Gold et al. |
| 5,763,566 A | 6/1998 | Jensen et al. |
| 5,789,157 A | 8/1998 | Jensen et al. |
| 5,840,867 A | 11/1998 | Toole et al. |
| 5,843,653 A | 12/1998 | Gold et al. |
| 5,861,254 A | 1/1999 | Schneider et al. |
| 5,864,026 A | 1/1999 | Jensen et al. |
| 5,874,218 A | 2/1999 | Drolet et al. |
| 5,945,527 A | 8/1999 | Tu et al. |
| 5,958,691 A | 9/1999 | Pieken |
| 6,013,443 A | 1/2000 | Heilig et al. |
| 6,114,120 A | 9/2000 | Jensen et al. |
| 6,127,119 A | 10/2000 | Stephens et al. |
| 6,232,462 B1 | 5/2001 | Collins et al. |
| 6,346,611 B1 | 2/2002 | Pagratis et al. |
| 6,376,474 B1 | 4/2002 | Heilig et al. |
| 6,613,526 B2 | 9/2003 | Heilig et al. |
| 6,734,172 B2 | 5/2004 | Scholler et al. |
| 6,897,015 B2 | 5/2005 | Henderson et al. |
| 7,855,054 B2 | 12/2010 | Schneider et al. |
| 7,947,447 B2 | 5/2011 | Zichi et al. |

(Continued)

FOREIGN PATENT DOCUMENTS

GB 2 183 661 6/1987
WO WO 89/06694 7/1989

(Continued)

OTHER PUBLICATIONS

Norris et al. Journal of Forensic Sciences 2007, vol. 52, pp. 800-805, abstract only, 3 pages total.*
ISR and Written Opinion mailed Dec. 10, 2012 in PCT/US2012/42835.
Sanders et al. (Jan. 2011) National Institute of Justice/NCJRS, Sperm Capture Using Aptamer Based Technology. NCJRS Final Technical report No. NCJ 236381.
Bigge and Mertes (1981) J. Org. Chem. 46(10): 1994-1997, "A palladium-catalyzed coupling reaction and a photolytic reaction for the direct synthesis of 5-arylpyrimidine nucleotides".

(Continued)

*Primary Examiner* — Tracy Vivlemore
(74) *Attorney, Agent, or Firm* — Swanson & Bratschun, L.L.C.

(57) ABSTRACT

The present disclosure describes the isolation, identification and purification of aptamers having sufficiently high affinity and specificity to capture and immobilize intact sperm cells in the presence of female epithelial cells and other non-sperm semen components. The present disclosure also describes affinity-based methods for the detection of sperm cells in samples, including from forensic sample surrogates consisting of swab eluates containing a mixture of HeLa cells and sperm cells. The present disclosure describes methods for eluting sperm cell samples from swabs; methods for purifying sperm cells and methods for amplification and analysis of male DNA. The affinity-based system described herein is inexpensive, simple to use and easily implemented in forensic laboratories.

8 Claims, 22 Drawing Sheets

(56) References Cited

U.S. PATENT DOCUMENTS

| | | | |
|---|---|---|---|
| 7,964,356 | B2 | 6/2011 | Zichi et al. |
| 2002/0009767 | A1 | 1/2002 | Muraca |
| 2002/0119473 | A1 | 8/2002 | Lupold |
| 2003/0162216 | A1 | 8/2003 | Gold et al. |
| 2003/0219801 | A1 | 11/2003 | Lipshutz |
| 2004/0106145 | A1 | 6/2004 | Gold et al. |
| 2004/0142384 | A1* | 7/2004 | Cohen et al. ............. 435/7.2 |
| 2004/0176282 | A1 | 9/2004 | Dalby et al. |
| 2005/0158780 | A1 | 7/2005 | Lupold et al. |
| 2005/0227225 | A1 | 10/2005 | Krevolin |
| 2005/0288244 | A1 | 12/2005 | Manoharan et al. |
| 2006/0057573 | A1 | 3/2006 | Gold et al. |
| 2006/0084130 | A1 | 4/2006 | Deslys et al. |
| 2006/0105341 | A1 | 5/2006 | Krause et al. |
| 2006/0199213 | A1 | 9/2006 | Capodieci et al. |
| 2007/0003950 | A1 | 1/2007 | Shen et al. |
| 2007/0041901 | A1 | 2/2007 | Diener et al. |
| 2007/0161015 | A1 | 7/2007 | Zheng et al. |
| 2007/0166742 | A1 | 7/2007 | Gold et al. |
| 2008/0261293 | A1 | 10/2008 | Garvin et al. |
| 2008/0318250 | A1 | 12/2008 | Gilmer et al. |
| 2009/0004667 | A1 | 1/2009 | Zichi et al. |
| 2009/0306461 | A1 | 12/2009 | Oksenberg et al. |
| 2010/0099149 | A1* | 4/2010 | Birnboim et al. ............. 435/91.3 |
| 2010/0317120 | A1 | 12/2010 | Heil et al. |
| 2011/0136099 | A1 | 6/2011 | Schneider et al. |
| 2011/0245479 | A1 | 10/2011 | Zichi et al. |
| 2012/0115752 | A1 | 5/2012 | Zichi et al. |

FOREIGN PATENT DOCUMENTS

| | | |
|---|---|---|
| WO | WO 92/14842 | 3/1992 |
| WO | WO 92/14843 | 9/1992 |
| WO | WO 94/06934 | 3/1994 |
| WO | WO 98/33941 | 8/1998 |
| WO | WO 02/44726 | 6/2002 |
| WO | WO 2004/043996 | 5/2004 |
| WO | WO 2006/096754 | 9/2006 |
| WO | WO 2008/021502 | 2/2008 |
| WO | WO 2011/006075 | 1/2011 |

OTHER PUBLICATIONS

Bock et al. (Mar. 2004) Proteomics 4(3):609-618, "Photoaptmaer arrays applied to multiplexed proteomic analysis".
Brody et al. (1999) Molecular Diagnostics 4(4):381-388, "The Use of Aptamers in Large Arrays for Molecular Diagnostics".
Conklin et al. (Jan. 2002) Journal of Surgical Research 102(1):13-21, "Shear stress regulates occluding and VEGF expression in procine or arterial endothelial cells".
Daniels et al. (Dec. 23, 2003) PNAS 100(26):15416-15421, "A tenascin-C aptamer identified by tumor cell SELEX: Systematic evolution of ligands by exponential enrichment".
Davis et al. (1978) The Lancet 1:1185-1187, "Scintigraphic Detection of Atherosclerotic Lesions and Venous Thrombi in Man by Indium-111-Labeled Autologous Platelets".
Davis et al. (May 1980) Circulation 61:982-988, "Scintigraphic Detection of Carotid Atherosclerosis with Indium-111-Labeled Autologous Platelets".
Davis et al. (Sep. 3, 2002) PNAS, 99(18):11616-11621, "Isolation of high-affinity GTP aptamers from partially structured RNA libraries".
DiDonato (2006) "Dissertation. Part II. Synthesis and Evaluation of Modified Nucleotides for DNA Aptamer Selection" University of North Carolina, Raleigh 30-53.
Drabovich et al. (May 1, 2006) Analytical Chemistry 78(9):3171-3178, "Selection of smart aptamers by methods of kinetic capillary electrophoresis".
Drolet et al. (Aug. 1996) Nature Biotechnology 14(8):1021-1025, "An enzyme-linked oligonucleotide assay".
Eaton et al. (1997) Bioorganic & Medicinal Chemistry 5(6):1087-1096, "Post-SELEX Combinatorial Optimization of Aptamers".
Ekins and Chu (Sep. 1997) JIFCC 9(3):100-109, "Immunoassay and Other Ligand Assays: Present Status and Future Trends".

Ellington & Szostak (1990) "Selection of RNAs with ligand-specific binding activity from pools of random sequence molecules" RNA Processing meeting abstract, p. 84.
EP Office Action issued Feb. 28, 2011 in European application serial No. 07718147.7.
EP Search report issued Feb. 22, 2010 in EP application serial No. 09012809.1.
Famulok and Szostak (1992) Angew. Chem. Int. Ed. Engl. 31(8): 979-988, "In Vitro Selection of Specific Ligand-binding Nucleic Acids".
Fischman et al. (1989) J. Nuc. Med. 30(6):1095-1100, "Radionuclide Imaging of Experimental Atherosclerosis with Nonspecific Polyclonal Immunoglobulin G".
Gebhardt et al. (Jun. 20, 2000) Biochemistry 39(24):7255-7265, "RNA aptamers to S-adenosylhomocysteine: kinectic properties, divalent cation dependency, and comparision with anti-S-adenosylhomocysteine antibody".
Ginsberg et al. (1990) Arteriosclerosis 10(2):256-262, "Noninvasive Imaging of 99mTechnetium-Labeled Low Density Lipoprotein Uptake by Tendon Xanthomas in Hypercholesterolemic Patients".
Gold et al. (Jan. 1, 1995) Harvey Lectures 91:47-57, "The SELEX Process: A Surprising Source of Therapeutic and Diagnostic Compounds".
Gold et al. (Jan. 1995) Annual Review of Biochemistry 64:763-797, "Diversity of Oligonucleotide Functions".
IPRP issued Jan. 19, 2012 in PCT/US2010/0041540.
Isaacsohn et al.(1986) Metabolism 35:364-366, "Adrenal Imaging With Technetium-99m-Labeled Low Density Lipoproteins".
ISR and Written Opinion mailed Dec. 17, 2008 in PCT/US2008/070383.
ISR and Written Opinion mailed Oct. 18, 2010 in PCT/US2010/041540.
Jellinek, et al. (Aug. 30, 1994) Biochemistry 33(34):10450-10456, "Inhibition of Receptor Binding by High-Affinity RNA Ligands to Vascular Endothelial Growth Factor".
Jhaveri et al. (Sep. 8, 1998) Bioorganic & Medicinal Chemistry Letters, 8(17):2285-2290, "In vitro selection of phosphorothiolated aptamers".
Joyce (1989) Gene 82:83-87, "Amplification, mutation and selection of catalytic RNA".
Joyce and Inoue (1989) Nucleic Acids Research 17(2): 711-722, "A novel technique for the rapid preparation of mutant RNAs".
Kang et al. (May 29, 2007) FEBS Letters, 581(13):2497-2502, "Combinatorial selection of a RNA thioaptamer that binds to Venezuelan equine encephalitis virus capsid protein".
Kawakami et al. (1997) Nucleic Acids Symposium Series No. 37:201-202, "Evolution of a phosphorothioate RNA library during in vitro selection".
Kinzler and Vogelstein (1989) Nucleic Acids Research 17(10): 3645-3653, "Whole genome PCR: application to the identification of sequences bound by gene regulatory proteins".
Kramer et al. (1974) J. Mol. Biol. 89: 719-736, "Evolution in vitro: sequence and phenotype of a mutant RNA resistant to ethidium bromide".
Langer et al. (Nov. 1981) Proc. Natl. Acad. Sci. USA,78(11):6633-6637, "Enzymatic synthesis of biotin-labeled polynucleotides: Novel nucleic acid affinity probes".
Lavitrano et al. (1992) Molecular Reproduction and Development 31:161-169, "The Interaction between Exogenous DNA and Sperm Cells".
Lees et al. (1983) J. Nuc. Med. 24:154-156, "External Imaging of Human Atherosclerosis".
Lees et al. (Sep-Oct. 1988) Arteriosclerosis 8:461-470, "Imaging Human Atherosclerosis with 99mTc-Labeled Low Density Lipoproteins".
Levisohn and Spiegleman (1968) PNAS USA 60: 866-872, "The cloning of a self-replicating RNA molecule".
Levisohn and Spiegleman (1969) PNAS USA 63: 805-811, "Further extracellular Darwinian experiments with replicating RNA moleucles: diverse variants isolated under different selective conditions".
McGown et al. (Nov. 1995) Anal. Chem. 67:663A-668A, "The Nucleic Acid Ligand. A New Tool for Molecular Recognition".

(56) References Cited

OTHER PUBLICATIONS

Mettinger et al. (Feb. 1978)The Lancet 1:242-244, "Detection of Atherosclerotic Plaques in Carotid Arteries by the Use of 123I-Fibrinogen".

Minar et al. (Jan. 1989) Stroke 20(1):27-33, "Indium-111-Labeled Platelet Scintigraphy in Carotid Atherosclerosis".

Moerlein et al. (Feb. 1991) J. Nuc. Med. 32(2):300-307, "Metabolic Imaging with Gallium-68-and Indium-111-Labeled Low-Density Lipoprotein".

Oliphant and Struhl (1987) Methods in Enzymology 155: 568-582, "The use of random-sequence oligonucleotides for determining consensus sequences".

Oliphant and Struhl (1988) Nucleic Acids Research 16(15): 7673-7683, "Defining the consensus sequences of E.coli promoter elements by random selection".

Oliphant et al. (1986) Gene 44:177-183, "Cloning of random-sequence oligodeoxynucleotides".

Oliphant et al. (Jul. 1989) Mol. Cell. Biol. 9: 2944-2949, "Defining the sequence specificity of DNA-binding proteins by selecting binding sites from random-sequence oligonucleotides: analysis of yeast GCN4 protein".

Ord et al. (1992) Circulation 85:288-297, "Imaging of Thrombi With Tissue-Type Plasminogen Activator Rendered Enzymatically Inactive and Conjugated to a Residualizing Label".

Osborne et al. (1997) Current Opinion in Chemical Biology 1:5-9, "Aptamers as Therapeutic and Diagnostic Reagents: Problems and Prospects".

Pinkel et al. (Dec. 1988) Proc. Natl. Acad. Sci. USA 85:9138-9142, "Fluorescence in situ hybridization with human chromosome-specific libraries: Detection of trisomy 21 and translocations of chromosome 4".

Ramos-Vara, J. (2005) Vet. Pathol. 42:405-426, "Technical Aspects of Immunohistochemistry".

Roberts et al. (1983) J. Lipid Research 24:1160-1167 "Selective Accumulation of Low Density Lipoproteins in Damaged Arterial Wall".

Robertson and Joyce (Mar. 1990) Nature 344: 467-468, "Selection in vitro of an RNA enzyme that specifically cleaves single-stranded DNA".

Seelig and Jaschke (1997) Tetrahedron Letters, 38(44):7729-7732, "Site-Specific Modification of Enzymatically Synthesized RNA: Transcription Initiation and Diels-Adler Reaction".

Syvanen et al. (1986) Nucleic Acid Research, 14(12):5037-5048, "Fast quantification of nucleic acid hybrids by affinity-based hybrid collection".

Szostak (1988) Redesigning the Molecules of Life, (S.A. Benner ed.) Springer-Verlag Berlin Heidelberg, pp. 87-113.

Tarasow (1998) Nucleic Acid Sciences 48(1):29-37, Dressed for Success"Realizing the Catalytic Potential of RNA".

Thiesen and Bach (Jun. 1990) Nucleic Acids Res. 18(11): 3203-3209, "Target detection assay (TDA): a versatile procedure to determine DNA binding sites as demonstrated on SP1 protein".

Tsai and Keene (Feb. 1993) J. Immunol. 150(3):1137-1145", In Vitro Selection of RNA Epitopes Using Autoimmune Patient Serum".

Tuerk and Gold (Aug. 1990) Science 249: 505-510, "Systematic evolution of ligands by exponential enrichment: RNA ligands to bacteriophage T4 DNA polymerase".

Tuerk et al. (Aug. 1992) Proc. Natl. Acad. Sci. USA 89:6988-6992, "RNA pseudoknots that inhibit human immunodeficiency virus type 1 reverse transcriptase".

Vaught, Jonathan David, Thesis Oct. 2008, "Enhancing the Functionality of Nucleic Acids".

Vaught et al. (Mar. 2010) J.Am. Chem. Soc. ePub, 132(12):4141-4151:4142, "Expanding the Chemistry of DNA for In Vitro Selection".

Zichi et al. (Mar. 7, 2008) Current Opinion in Chemical Biology 12(1):78-85, "Proteomics and diagnostics: Let's Get Specific, again".

Gold et al. (Dec. 7, 2010) PLOS ONE 5(12):e15004, "Aptamer-Based Multiplexed Proteomic Technology for Biomarker Discovery".

* cited by examiner

METHOD FOR PURIFICATION AND IDENTIFICATION OF SPERM CELLS

RELATED APPLICATIONS

This application claims priority to U.S. Provisional Application Ser. No. 61/498,224, filed Jun. 17, 2011.

FIELD OF THE INVENTION

The present disclosure relates generally to the field of nucleic acids and more particularly to aptamers capable of binding to intact human sperm cells. More specifically, the present disclosure relates to aptamers with sufficiently high affinity and specificity to capture and immobilize intact sperm cells in the presence of female epithelial cells and other non-sperm semen components.

Incorporated by reference herein in its entirety is the Sequence Listing entitled "sequence listing.txt", created Jun. 15, 2012 size 3 of kilobytes

BACKGROUND

The following description provides a summary of information relevant to the present disclosure and is not a concession that any of the information provided or publications referenced herein is prior art to the claimed invention.

A key form of evidence in modern sexual assault cases is a DNA profile originating from the perpetrator. Such evidence is generally obtained from swabs taken in the course of forensic examination of victims. These swabs are typically heavily contaminated with epithelial cells from the victim as well as bearing semen from the perpetrator. The vast excess of released DNA from the victim's cells can interfere with generation of a clean DNA profile from the perpetrator, therefore a purification step is required to separate contaminating epithelia from sperm cells. Currently, the most common protocol is the so-called differential extraction (DE) procedure (Gill et al. (1985) Nature, 318(6046):577-579; Yoshida et al. (1995) Forensic Sci Int, 72(11:25-33). This method relies on differential lysis of sperm and epithelial cells in sodium dodecyl sulfate (SDS). In spite of its simplicity, it is time consuming, labor intensive, difficult to automate and can result in possible DNA mixtures when sperm head counts are low.

A variety of methods described in the literature are aimed at improving or modifying the differential extraction procedure to achieve better sperm separation from contaminating victim DNA (Voorhees et al. (2006) J Forensic Sci, 51(3): 574-579; Ladd et al. (2006) NCJRS (www.ncjrs.gov/pdffiles1/nij/grants/215339.pdf); Garvin et al. (2009) J Forensic Sci, 54(6):1297-1303). Microfluidic devices have been created which exploit the differential physical properties of sperm cells versus other cells and also allow for direct silica-based DNA extraction (Horsman et al. (2005) Anal Chem, 77(3):742-749; Bienvenue et al. (2006) J Forensic Sci, 51(2): 266-273). Multiple publications describe the uses of laser microdissection to selectively capture and isolate sperm cells (Di Martino et al. (2004) Forensic Sci Int, 146 Suppl:S151-153; Elliott et al. (2003) Forensic Sci Int 137(1):28-36; Sanders et al. (2006) J Forensic Sci, 51(4):748-757). This method uses an optical microscope fitted with a laser beam to capture cells of interest from cell smears. This method offers high specificity and allows the use of limited numbers of spermatozoa on microscope slides for DNA extraction and Forensic Short Tandem Repeat (STR) analysis. However, this system is expensive; process is time-consuming, labor-intensive and not easily amenable to automation.

An automated format for the differential extraction process has been developed by Promega Corporation. The Differex system allows the processing of up to 48 samples in parallel using 96 well microtiter plates and robotic pipetting system such as Biomek 2000 from Beckman Coulter. However, this platform has not gained popularity, perhaps due to the high cost of an appropriate automation platform. Moreover, the necessity for minimization of the risk of cross-contamination and misidentification of samples essentially precludes use of an open 96-well plate. Improved methods that allow the forensic analyst to process samples individually are clearly needed.

One approach that bypasses the selective lysis and extensive cell washing by centrifugation used in differential extraction processes is to physically separate sperm cells away from intact epithelial cells. Cell sorting using flow cytometry has been demonstrated (Schoell et al. (1999) Obstet Gynecol, 94(4):623-627); Schoell et al. (1999) Cytometry, 36(4):319-323; however, it is unlikely that this technique would be widely used to casework due to cost of FACS instruments with cell sorting capacity and the difficulty in operating them. Sperm cell separation from epithelial cells can also be achieved using size filtration, for example, sperm can be physically separated from much larger epithelial cells using 10 micrometer filter (Chen et al. (1998) J Forensic Sci, 43(1): 114-118, or sperm can be retained using 2 micrometer filter if epithelial cells are lysed (Ladd et al. (2006) NCJRS (www.ncjrs.gov/pdffiles1/nij/grants/215339.pdf); Garvin, A. M. (2003) J Forensic Sci, 48(5):1084-1087). These filtration methods still require centrifugation, and filters are susceptible to clogging and inefficient cell recovery. Moreover, they do not provide male DNA fractions that are as good or better that those generated by the standard differential extraction method. Laser microdissection of sperm cells from slides has been also demonstrated (Di Martino et al. (2004) Forensic Sci Int, 146 Suppl:S151-153; Elliott et al. (2003) Forensic Sci Int 137(1):28-36; Sanders et al. (2006) J Forensic Sci, 51(4):748-757). This method allows for highly specific isolation of cells, however, this method is unlikely to be widely adopted for forensic casework analysis due to the high cost of the necessary instrumentation.

Affinity purification of sperm cells is in principle one of the simplest, most intuitive, and accessible methods for processing of forensic samples. Indeed, affinity purification using antibodies to various sperm cell surface antigens has been demonstrated (Eisenberg, A. (2002) NCJRS (www.ncjrs.gov/pdffiles1/nij/grants/197532.pdf). However, this approach suffered from low efficiency, as captured cells tended to be lost in wash steps. Photocrosslinking of antibody and antigen was utilized to improve complex retention; however, this approach requires chemical modification of antibodies and has not gained popularity in actual forensic applications. Antibody epitope stability is another problem with this approach, because detergents typically used for swab elution (SDS or Sarkosyl) denature epitopes recognized by anti-sperm antibodies.

SUMMARY

The present disclosure provides methods, devices, reagents, and kits designed to detect the presence of sperm cells in a sample. Samples may be in the form of cotton swabs or other materials used in rape kits, or other evidence collected that contains sperm cells found in combination with other materials. The methods of the of the instant disclosure enable rapid and facile separation of spermatozoa from female epithelial cells in mixed sexual assault evidence, and enables amplification and analysis of male DNA. The technology is intended to be cost-effective, high-throughput, commercially viable, and be easily implemented in forensic laboratories.

In one embodiment, the present disclosure generally describes methods for the purifying sperm cell sperm cells in a sample comprising contacting said sample with an aptamer (or photoaptamer) that binds to sperm cells, thereby forming aptamer-sperm cell affinity complexes; partitioning the aptamer-sperm cell affinity complexes from the remainder of the sample; and detecting and/or quantifying and/or characterizing various genetic loci of the purified sperm cells for identification purposes. In one embodiment, the method comprises contacting an aptamer having specific affinity for sperm cells and comprising a detectable moiety with a sample, optionally introducing a slow off-rate enrichment process; partitioning bound nucleic acid-sperm cell complexes from the remainder of the sample and detecting and/or quantifying said purified sperm cells by means of the detectable moiety.

In another embodiment, an aptamer that has a specific affinity for sperm cells and comprising a tag supporting specific binding to a solid support is immobilized on a solid support in solution prior to equilibration with the sample. The attachment of the aptamer to the solid support is accomplished by contacting the solid support with the aptamer and allowing the tag included on the aptamer to associate, either directly or indirectly, with an appropriate capture agent that is attached to the solid support. In some embodiments, the method further comprising washing with a solution buffered to pH11 to remove aptamer/aptamer aggregates, thereby reducing assay background.

In one embodiment the tag is biotin and the solid support is streptavidin beads. Other possible tag/support combinations include, but are not limited to hexahistidine (tag) and nickel or cobalt-nitrilotriacetic acid-substituted magnetic beads (support). A tag may also be selected from a primary amine appended to the aptamer, which would support covalent binding to commonly available supports, e.g. carboxyl-substituted magnetic beads. Other tags include, but are not limited to a dye, a hapten, a digoxigenin; the solid supports can be selected from solid support modified with an appropriate capture agent for the respective tag.

A sample is then prepared and contacted with the immobilized aptamers that have a specific affinity for sperm cells. If the sample contains sperm cells, an aptamer-sperm cell affinity complex will form in the mixture with the sample. A slow off-rate enrichment process is optionally introduced to induce the dissociation of nucleic acid-target complexes with relatively fast dissociation rates. The aptamer-sperm cell affinity complex and uncomplexed aptamer that has associated with the probe on the solid support is then partitioned from the remainder of the mixture, thereby removing all uncomplexed matter in the sample (sample matrix); i.e., components of the mixture not associated with the solid support. Following partitioning, the sperm cells are released from the aptamer thereby allowing detection and/or quantification.

In one embodiment, the sperm cells are quantified by lysing the sperm cells and measuring the amount of DNA in the lysate. The sperm cells can also be quantified using a cytometer or any other methods that would be known to those skilled in the art.

In one embodiment the sample is prepared by stripping the sperm cells of their plasma membrane prior to contacting with the aptamer. This method comprises treating said sample with a buffered detergent prior to performing the affinity based assay. In one embodiment the detergent is selected from an anionic detergent. In one embodiment the anionic detergent is selected from the group including, but not limited Triton X-200, sodium deoxycholate, lithium dodecyl sulfate (LDS) and sodium dodecyl sulfate (SDS).

In another aspect the method for purification of sperm cells in a sample comprises preparing a mixture by contacting the sample with an aptamer comprising a tag and having specific affinity for sperm cells, wherein an aptamer-sperm cell affinity complex is formed if sperm cells are present in said sample, optionally introducing a slow off-rate enrichment process to induce the dissociation of nucleic acid-target complexes with relatively fast dissociation rates; exposing the mixture to a solid support comprising a capture element; allowing the tag to associate with the capture element; partitioning the solid support from the remainder of the mixture, thereby removing all uncomplexed matter in the sample (sample matrix); i.e., components of the mixture not associated with the solid support; and detecting and/or quantifying the purified sperm cells.

The present disclosure also describes a method for eluting sperm cells from a swab, said method comprising contacting said swab with a buffered detergent solution. In one embodiment, the detergent is an anionic detergent. In some aspects, the detergent is selected from the group including, but not limited to Triton X-200, sodium deoxycholate and lithium dodecyl sulfate (LDS). In one embodiment, the swab is selected from the group including, but not limited to a Dacron swab, a flocked nylon swab and a cotton swab.

The present disclosure further describes methods for the isolation and purification of sperm cells from solution, comprising immobilizing an aptamer comprising a tag that has a specific affinity for sperm cells on a solid support in solution, contacting said aptamer with the sperm cell solution; wherein an aptamer-sperm cell affinity complex is formed; partitioning said complex from the remainder of the solution; and releasing said sperm cells from the support bound aptamer. In some embodiments, the bound sperm cells are lysed allowing analysis of the released DNA.

The present disclosure further describes methods for identifying and producing aptamers to sperm cells. In some embodiments, the methods utilize the modified SELEX process for generating slow off-rate (slow rate of dissociation) aptamers. In one embodiment, the method comprises preparing a candidate mixture of nucleic acids; contacting the candidate mixture with a sperm cell sample wherein nucleic acids with the highest relative affinities to the target preferentially bind the target, forming nucleic acid-target complexes; optionally introducing a slow off-rate enrichment process to induce the dissociation of nucleic acid-target complexes with relatively fast dissociation rates; partitioning the remaining bound nucleic acid-target complexes from free nucleic acids in the candidate mixture; and identifying and/or producing the nucleic acids that were bound to the sperm cells. The process may further include the iterative step of amplifying the nucleic acids that bind to the target to yield a mixture of nucleic acids enriched with nucleic acids that bind to the target molecule yet produce nucleic acid-target molecule complexes having slow dissociation rates.

In another embodiment, the candidate mixture of nucleic acids includes nucleotide residues containing modified nucleotide bases that may aid in the formation of modified nucleic acid-target complexes having slow dissociation rates.

In yet another embodiment, an extension of the SELEX process for identifying aptamers and slow off-rate aptamers, termed counter-SELEX is employed. Counter-SELEX is a method for improving the specificity of nucleic acid ligands to a target molecule by eliminating nucleic acid ligand sequences with cross-affinity to one or more non-target molecules.

In one embodiment, the aptamers are produced with a detectable moiety and may be directly detected after binding with their respective target or targets following an optional wash step to remove unreacted aptamer. In other embodiments, the one or more slow off-rate aptamers interaction with their respective target or targets is detected after the two components of an element to support signal generation are reacted.

The disclosure includes slow off-rate aptamers identified and produced according to said methods.

In yet another embodiment, the present disclosure describes the isolation of sperm from a mixture of sperm and HeLa cells, which serve as a surrogate for human female epithelial cells.

The methods of the of the instant disclosure enable rapid and facile separation of spermatozoa from female epithelial cells in mixed sexual assault evidence, and supports amplification and genetic analysis of male DNA. The technology is intended to be cost-effective, high-throughput, commercially viable, and be easily implemented in forensic laboratories.

In one embodiment, kits using aptamer reagents can be prepared based on the methods disclosed herein.

BRIEF DESCRIPTION OF THE FIGURES

FIG. 11A shows the profile of the mixed sample eluted from the swab prepared from a mixture of HeLa cells and semen. FIG. 11B shows the profile of the DNA isolated from cells purified using sperm-specific aptamer-coated magnetic beads. FIG. 11C shows the profile of a HeLa cell-only DNA control and FIG. 11D shows the profile of a sperm DNA-only control.

FIG. 12A shows beads coated with aptamer ID number 4105-1 binding preferentially to the tail region of the sperm. FIG. 12B shows beads coated with aptamer ID 4105-10. FIGS. 12C and 12D show beads coated with aptamer ID 4105-257 and 4105-365, respectively, binding to both tail and head of sperm cell.

DETAILED DESCRIPTION

Figure 1:
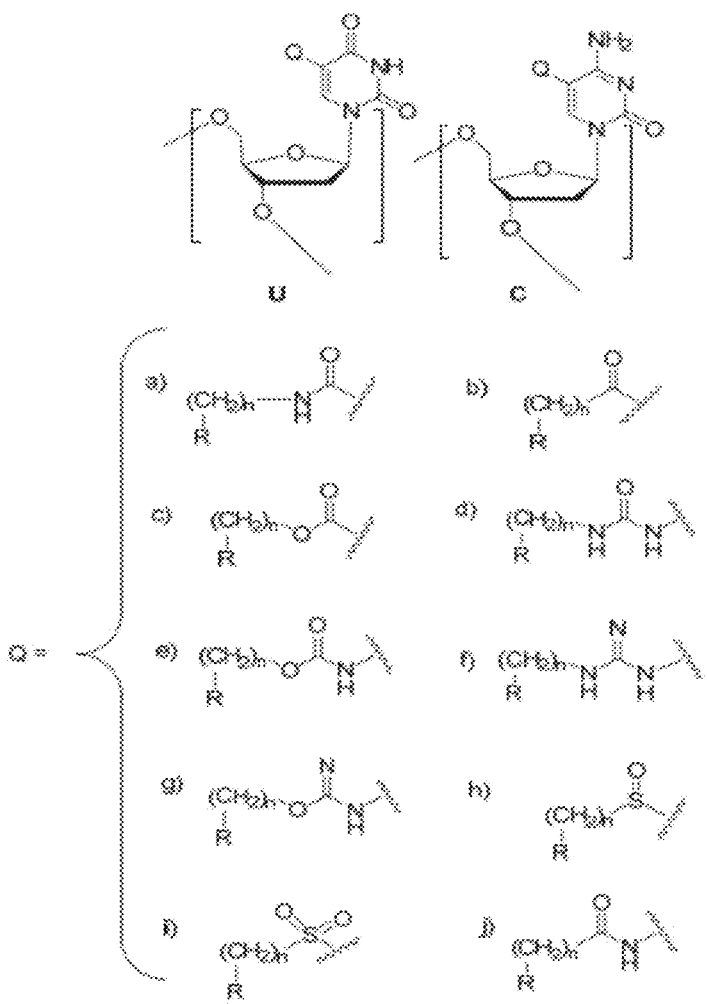
FIG. 1 illustrates C-5 pyrimidine modifications to prepare aptamers of the present invention.
Figure 1:
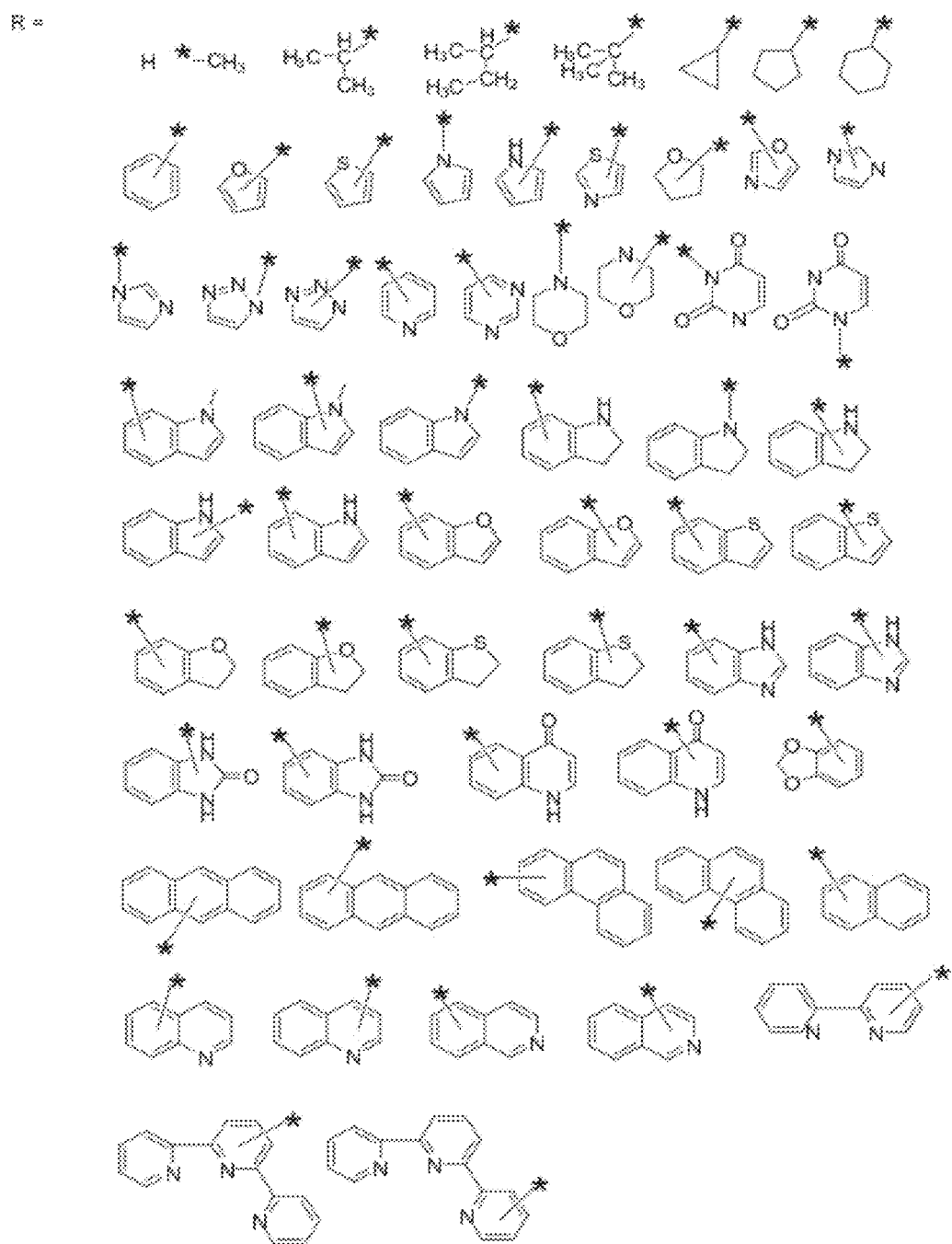
Figure 1:
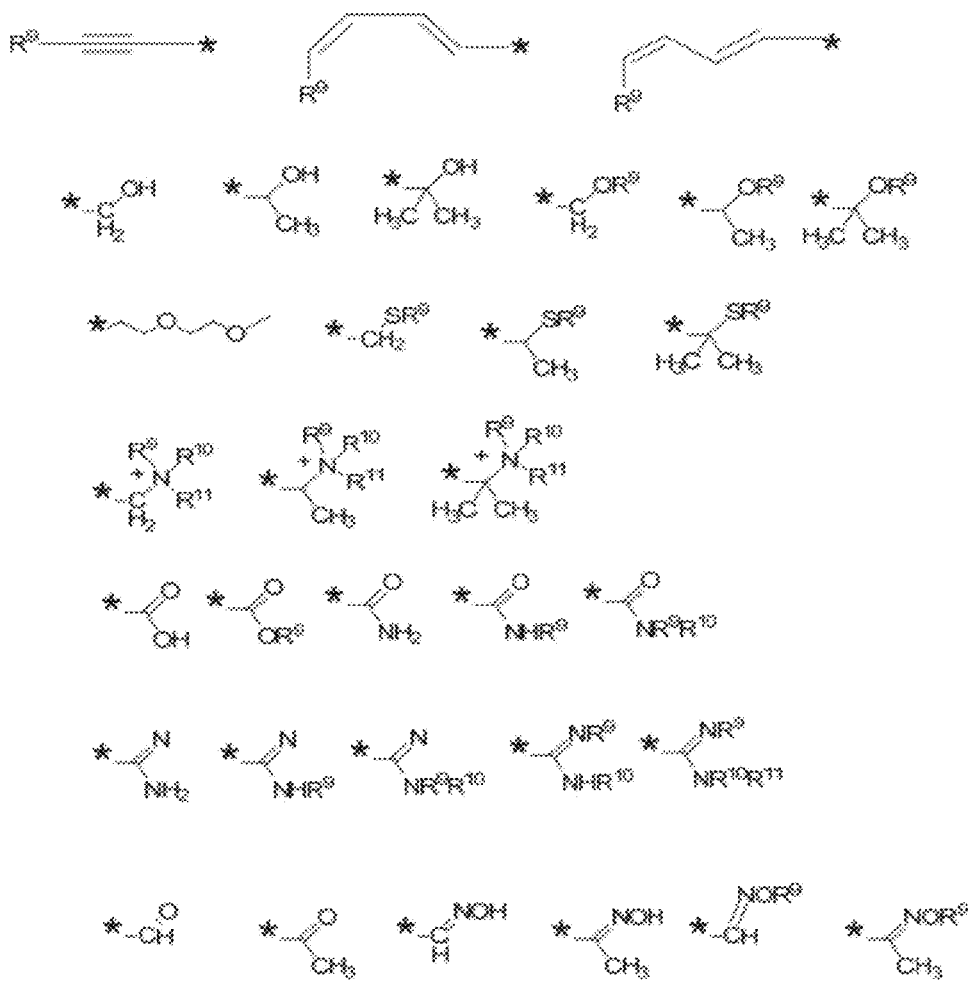

Reference will now be made in detail to representative embodiments of the invention. While the invention will be described in conjunction with the enumerated embodiments, it will be understood that the invention is not intended to be limited to those embodiments. On the contrary, the invention is intended to cover all alternatives, modifications, and equivalents that may be included within the scope of the present invention as defined by the claims.

The practice of the invention disclosed herein employs, unless otherwise indicated, conventional methods of chemistry, microbiology, molecular biology, and recombinant DNA techniques within the level of skill in the art. Such techniques are explained fully in the literature. See, e.g., Sambrook, et al. *Molecular Cloning: A Laboratory Manual* (Current Edition); *DNA Cloning: A Practical Approach*, vol. I & II (D. Glover, ed.); Oligonucleotide Synthesis (N. Gait, ed., Current Edition); *Nucleic Acid Hybridization* (B. Hames & S. Higgins, eds., Current Edition); *Transcription and Translation* (B. Hames & S. Higgins, eds., Current Edition; Histology for Pathologists (S. E. Mills, Current Edition).

All publications, published patent documents, and patent applications cited in this specification are indicative of the level of skill in the art(s) to which the invention pertains. All publications, published patent documents, and patent applications cited herein are hereby incorporated by reference to the same extent as though each individual publication, published patent document, or patent application was specifically and individually indicated as being incorporated by reference. Examples in cited publications and limitations related therewith are intended to be illustrative and not exclusive. Other limitations of the cited publications will become apparent to those of skill in the art upon a reading of the specification and a study of the drawings.

Unless defined otherwise, technical and scientific terms used herein have the same meaning as commonly understood by one of ordinary skill in the art(s) to which this invention belongs. Although any methods, devices, and materials similar or equivalent to those described herein can be used in the practice or testing of the invention, the preferred methods, devices and materials are now described.

The present disclosure includes methods, devices, reagents, and kits designed to capture and purify sperm cells.

The disclosed methods, devices, reagents, and kits provide high sensitivity assays for the detection and/or purification of sperm cells in a sample.

It is noteworthy that, unless otherwise specified in a particular embodiment, the methods described herein are independent of the specific order in which the steps are described. For purposes of illustration, the methods are described as a specific sequence of steps; however, it is to be understood that any number of permutations of the specified sequence of steps is possible, so long as the objective of the particular assay being described is accomplished. Stated another way, the steps recited in any of the disclosed methods may be performed in any feasible order, and the methods of the invention are not limited to any particular order presented in any of the described embodiments, the examples, or the appended claims. Further, for convenience and ease of presentation, the various methods are described with reference to a single target molecule and a single aptamer. However, it is to be understood that any of the described methods can be performed in a multiplex format that can provide for the simultaneous detection and/or quantification of multiple targets using multiple aptamers, such that, for example, multiple target molecules in a test sample can be detected and/or quantified by contacting the sample with multiple aptamers, wherein each aptamer has a specific affinity for a particular target molecule (i.e., in a multiplex format).

As used in this specification, including the appended claims, the singular forms "a," "an," and "the" include plural references, unless the content clearly dictates otherwise, and are used interchangeably with "at least one" and "one or more." Thus, reference to "an aptamer" includes mixtures of aptamers, reference to "a probe" includes mixtures of probes, and the like.

As used herein, the term "about" represents an insignificant modification or variation of the numerical values such that the basic function of the item to which the numerical value relates is unchanged.

As used herein, the terms "comprise," "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but may include other elements not expressly listed or inherent to such process, method, product-by-process, or composition of matter.

As used herein, the term "nucleotide" refers to a ribonucleotide or a deoxyribonucleotide, or a modified form thereof, as well as an analog thereof. Nucleotides include species that include purines (e.g., adenine, hypoxanthine, guanine, and their derivatives and analogs) as well as pyrimidines (e.g., cytosine, uracil, thymine, and their derivatives and analogs).

As used herein, "nucleic acid," "oligonucleotide," and "polynucleotide" are used interchangeably to refer to a polymer of nucleotides and include DNA, RNA, DNA/RNA hybrids and modifications of these kinds of nucleic acids, oligonucleotides and polynucleotides, wherein the attachment of various entities or moieties to the nucleotide units at any position are included. The terms "polynucleotide," "oligonucleotide," and "nucleic acid" include double- or single-stranded molecules as well as triple-helical molecules.

Nucleic acid, oligonucleotide, and polynucleotide are broader terms than the term aptamer and, thus, the terms nucleic acid, oligonucleotide, and polynucleotide include polymers of nucleotides that are aptamers, but the terms nucleic acid, oligonucleotide, and polynucleotide are not limited to aptamers.

As used herein, the terms "modify", "modified", "modification", and any variations thereof, when used in reference to an oligonucleotide, means that at least one of the four constituent nucleotide bases (i.e., A, G, T/U, and C) of the oligonucleotide is an analog or ester of a naturally occurring nucleotide. In some embodiments, the modified nucleotide confers nuclease resistance to the oligonucleotide. In some embodiments, the modified nucleotides lead to predominantly hydrophobic interactions of aptamers with protein targets resulting in high binding efficiency and stable co-crystal complexes. A pyrimidine with a substitution at the C-5 position is an example of a modified nucleotide. Modifications can include backbone modifications, methylations, unusual base-pairing combinations such as the isobases isocytidine and isoguanidine, and the like. Modifications can also include 3' and 5' modifications, such as capping. Other modifications can include substitution of one or more of the naturally occurring nucleotides with an analog, inter-nucleotide modifications such as, for example, those with uncharged linkages (e.g., methyl phosphonates, phosphotriesters, phosphoamidates, carbamates, etc.) and those with charged linkages (e.g., phosphorothioates, phosphorodithioates, etc.), those with intercalators (e.g., acridine, psoralen, etc.), those containing chelators (e.g., metals, radioactive metals, boron, oxidative metals, etc.), those containing alkylators, and those with modified linkages (e.g., alpha anomeric nucleic acids, etc.). Further, any of the hydroxyl groups ordinarily present on the sugar of a nucleotide may be replaced by a phosphonate group or a phosphate group; protected by standard protecting groups; or activated to prepare additional linkages to additional nucleotides or to a solid support. The 5' and 3' terminal OH groups can be phosphorylated or substituted with amines, organic capping group moieties of from about 1 to about 20 carbon atoms, polyethylene glycol (PEG) polymers in one embodiment ranging from about 10 to about 80 kDa, PEG polymers in another embodiment ranging from about 20 to about 60 kDa, or other hydrophilic or hydrophobic biological or synthetic polymers. In one embodiment, modifications are of the C-5 position of pyrimidines. These modifications can be produced through an amide linkage directly at the C-5 position or by other types of linkages.

Polynucleotides can also contain analogous forms of ribose or deoxyribose sugars that are generally known in the art, including 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. As noted above, one or more phosphodiester linkages may be replaced by alternative linking groups. These alternative linking groups include embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. Substitution of analogous forms of sugars, purines, and pyrimidines can be advantageous in designing a final product, as can alternative backbone structures like a polyamide backbone, for example.

As used herein, the term "C-5 modified pyrimidine" refers to a pyrimidine with a modification at the C-5 position including, but not limited to, those moieties illustrated in FIG. 1. Examples of a C-5 modified pyrimidine include those described in U.S. Pat. Nos. 5,719,273 and 5,945,527. Examples of a C-5 modification include substitution of deoxyuridine at the C-5 position with a substituent independently selected from: benzylcarboxyamide (alternatively benzylaminocarbonyl) (Bn), naphthylmethylcarboxyamide (alternatively naphthylmethylaminocarbonyl) (Nap), tryptaminocarboxyamide (alternatively tryptaminocarbonyl) (Trp), phenethylcarboxyamide (alternatively phenethylamino carbonyl) (Pe), thiophenylmethylcarboxyamide (alternatively thiophenylmethylaminocarbonyl) (Th) and isobutylcarboxyamide (alternatively isobutylaminocarbonyl) (iBu) as illustrated immediately below.

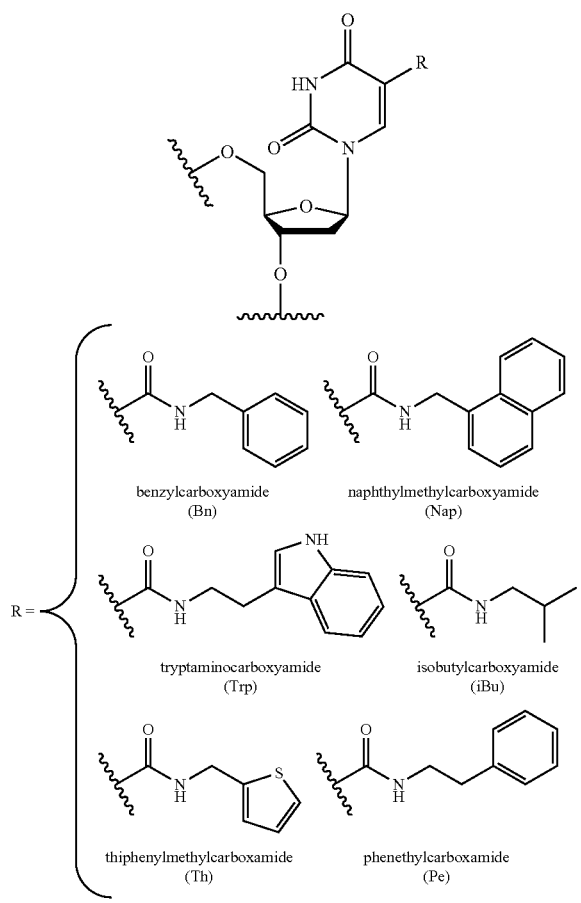

Chemical modifications of a C-5 modified pyrimidine can also be combined with, singly or in any combination, 2'-position sugar modifications, modifications at exocyclic amines, and substitution of 4-thiouridine and the like.

Representative C-5 modified pyrimidines include: 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-isobutylcarboxyamide)-2'-deoxyuridine (iBudU), 5-(N-isobutylcarboxyamide)-2'-O-methyluridine, 5-(N-phenethylcarboxyamide)-2'-deoxyuridine (PedU), 5-(N-thiophenylmethylcarboxyamide)-2'-deoxyuridine (ThdU), 5-(N-isobutylcarboxyamide)-2'-fluorouridine, 5-(N-tryptaminocarboxyamide)-2'-deoxyuridine (TrpdU), 5-(N-tryptaminocarboxyamide)-2'-O-methyluridine, 5-(N-tryptaminocarboxyamide)-2'-fluorouridine, 5-(N-[1-(3-trimethylamonium) propyl]carboxyamide)-2'-deoxyuridine chloride, 5-(N-naphthylmethylcarboxyamide)-2'-deoxyuridine (NapdU), 5-(N-naphthylmethylcarboxyamide)-2'-O-methyluridine, 5-(N-naphthylmethylcarboxyamide)-2'-fluorouridine or 5-(N-[1-(2,3-dihydroxypropyl)]carboxyamide)-2'-deoxyuridine).

Nucleotides can be modified either before or after synthesis of an oligonucleotide. A sequence of nucleotides in an oligonucleotide may be interrupted by one or more non-nucleotide components. A modified oligonucleotide may be further modified after polymerization, such as, for example, by conjugation with any suitable labeling component.

As used herein, the term "at least one pyrimidine," when referring to modifications of a nucleic acid, refers to one, several, or all pyrimidines in the nucleic acid, indicating that any or all occurrences of any or all of C, T, or U in a nucleic acid may be modified or not.

As used herein, "nucleic acid ligand" "aptamer" and "clone" are used interchangeably to refer to a non-naturally occurring nucleic acid that has or may have a desirable action on a target molecule. A desirable action includes, but is not limited to, binding of the target, catalytically changing the target, reacting with the target in a way that modifies or alters the target or the functional activity of the target, covalently attaching to the target (as in a suicide inhibitor), and facilitating the reaction between the target and another molecule. In one embodiment, the action is specific binding affinity for a target molecule, such target molecule being a three dimensional chemical structure, other than a polynucleotide, that binds to the aptamer through a mechanism which is predominantly independent of Watson/Crick base pairing or triple helix binding, wherein the aptamer is not a nucleic acid having the known physiological function of being bound by the target molecule. Aptamers include nucleic acids that are identified from a candidate mixture of nucleic acids, the aptamer being a ligand of a given target, by the method comprising: (a) contacting the candidate mixture with the target, wherein nucleic acids having an increased affinity to the target relative to other nucleic acids in the candidate mixture may be partitioned from the remainder of the candidate mixture; (b) partitioning the increased affinity and/or slow off-rate nucleic acids from the remainder of the candidate mixture; and (c) amplifying the increased affinity and/or slow off-rate nucleic acids to yield a ligand-enriched mixture of nucleic acids, whereby aptamers to the target molecule are identified. It is recognized that affinity interactions are a matter of degree; however, in this context, the "specific binding affinity" of an aptamer for its target means that the aptamer binds to its target generally with a much higher degree of affinity than it binds to other, non-target, components in a mixture or sample. An aptamer can include any suitable number of nucleotides. Different aptamers may have either the same number or a different number of nucleotides. Aptamers may be DNA or RNA and may be single stranded, double stranded, or contain double stranded regions.

As used herein, the terms "purify," "purification," "purifying," refer to methods to enrich, enhance or concentrate the number of sperm cells in a sample relative to contaminating species. For example, in the course of the forensic examination of female victims of rape the number of sperm cells in the sample may be significantly lower than the number of female epithelial cells (for example, approximately 1:1000). Thus, the goal of "purification" as used herein is enhance, enrich or concentrate the number of sperm cells relative to the number of female epithelial cells to enable easier detection. Thus, as used herein the terms "purify," "purification," "purifying," refer to methods for concentrating, enriching or enhancing the number of sperm cells in such a sample to a level that is more easily detectable. Thus, in certain embodiments the level of purification of the sperm cells relative to female epithelial cells may result in an improved ratio for detection or quantification, for example, to: about 100:1; about 50:1 about 25:1; about 10:1; or about 1:1 or even greater.

As used herein, a "SOMAmer" or "Slow Off-Rate Aptamer" refers to an aptamer having improved off-rate characteristics. Slow off-rate aptamers can be generated using the modified SELEX methods described in U.S. Publication No. 20090004667, entitled "Method for Generating Aptamers with Improved Off-Rates." The methods disclosed herein are in no way limited to slow off-rate aptamers, however, use of the slow off-rate process described in U.S. Pat. No. 7,964,356 and U.S. Publication No. 2012/0115752, may provide improved results.

As used herein, "slow off-rate" or "slow rate of dissociation" or "slow dissociation rate" refers to the time it takes for an aptamers/target complex to begin to dissociate. This can be expressed as a half life, $t_{1/2}$, or the point at which 50% of the aptamer/target complex has dissociated. The off-rate or dissociation rate of a slow off-rate aptamer, expressed as $t_{1/2}$ values, can be ≥ about 15 min., ≥ about 30 min., ≥ about 60 min., ≥ about 90 min., ≥ about 120 min. ≥ about 150 min. ≥ about 180 min. ≥ about 210 min., and ≥ about 240 min.

The SELEX Process

"SELEX" refers to a process that combines the selection of nucleic acids that interact with a target in a desirable manner (e.g., binding to a protein) with the amplification of those selected nucleic acids. Optional iterative cycling of the selection/amplification steps allows selection of one or a small number of nucleic acids that interact most strongly with the target from a pool that contains a very large number of nucleic acids. Cycling of the selection/amplification procedure is continued until a selected goal is achieved. The SELEX methodology is described in the SELEX Patents. See, e.g., U.S. Pat. No. 5,475,096, entitled "Nucleic Acid Ligands." The SELEX process can be used to generate an aptamer that covalently binds its target as well as an aptamer that non-covalently binds its target. See, e.g., U.S. Pat. No. 5,705,337 entitled "Systematic Evolution of Nucleic Acid Ligands by Exponential Enrichment Chemi-SELEX," and U.S. Pat. No. 5,763,177, entitled Systematic Evolution of Ligands by Exponential Enrichment: Photoselection of Nucleic Acid Ligands and Solution SELEX."

SELEX generally includes preparing a candidate mixture of nucleic acids, binding of the candidate mixture to the desired target molecule to form an affinity complex, separating the affinity complexes from the unbound candidate nucleic acids, separating and isolating the nucleic acid from the affinity complex, purifying the nucleic acid, and identifying a specific aptamer sequence. The process may include multiple rounds to further refine the affinity of the selected aptamer. The process can include amplification steps at one or more points in the process.

Figure 2:
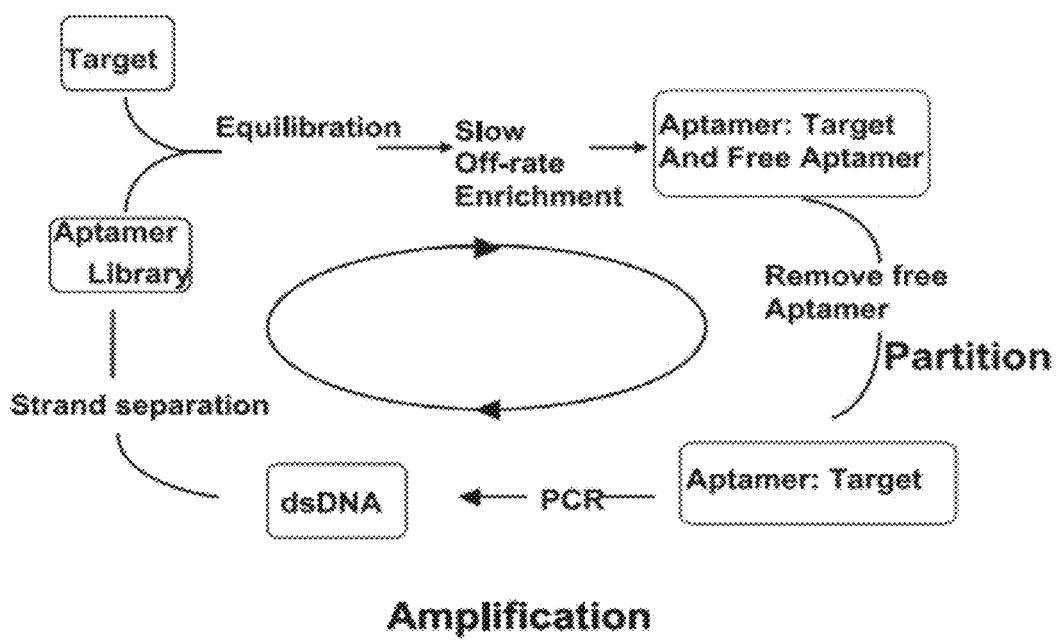
FIG. 2 illustrates an exemplary SELEX method which includes the step of incorporating a slow off-rate enrichment process.

SELEX can also be used to identify aptamers that have desirable off-rate characteristics, also referred to herein as "slow off-rate aptamers". See U.S. Pat. No. 7,947,447, entitled "Method for Generating Aptamers with Improved Off-Rates," which describes improved SELEX methods for generating aptamers that can bind to target molecules. Methods for producing aptamers and photoaptamers having slower rates of dissociation from their respective target molecules are described. With reference to FIG. 2 the improved SELEX process includes the introduction of a slow off-rate enrichment process following equilibration of the candidate mixture of nucleic acids with the target or targets and a partitioning step prior to subsequent steps in the SELEX process.

Introduction of a slow off-rate enrichment process to the basic SELEX process provides a means for enrichment of aptamer affinity complexes with slow dissociation rates from a set of nucleic acid-target complexes that includes a variety of dissociation rates. Thus, the improved SELEX process provides a method for identifying aptamers that bind target molecules and, once bound, have relatively slow rates of dissociation (also referred to herein as "off-rates") from the target molecule. The methods include the use of modified nucleotides in the production of candidate nucleic acid mixtures to generate aptamers with improved off-rate performance (see also U.S. Pat. No. 7,855,054).

As used herein, "candidate mixture" is a mixture of nucleic acids of differing sequence from which to select a desired ligand. The source of a candidate mixture can be from naturally-occurring nucleic acids or fragments thereof, chemically synthesized nucleic acids, enzymatically synthesized nucleic acids or nucleic acids made by a combination of the foregoing techniques. The nucleic acid candidate mixture can be modified in various ways to enhance the probability of the nucleic acids having facilitating properties or other desirable properties, particularly those that enhance the interaction between the nucleic acid and the target. In addition, a SELEX process can be used to produce a candidate mixture, that is, a first SELEX process experiment can be used to produce a ligand-enriched mixture of nucleic acids that is used as the candidate mixture in a second SELEX process experiment. A candidate mixture can also comprise nucleic acids with one or more common structural motifs. As used herein, a candidate mixture is also sometimes referred to as a "pool" or a "library." For example, an "RNA pool" refers to a candidate mixture comprised of RNA.

In various embodiments, the candidate mixture includes nucleic acid sequences having variable regions that include modified groups. The modified groups can be modified nucleotide bases. The variable region can contain fully or partially random sequences; it can also contain sub-portions of a fixed sequence that is incorporated within the variable region. The nucleotides within the fixed regions can also contain modified nucleotide bases, or they can contain the standard set of naturally occurring bases.

As used herein, "modified nucleic acid" refers to a nucleic acid sequence containing one or more modified nucleotides. In some embodiments it may be desirable that the modified nucleotides are compatible with the SELEX process. Certain modified aptamers may be used in any of the described methods, devices, and kits described herein. These modified nucleotides have been shown to produce novel aptamers that have very slow off-rates from their respective targets while maintaining high affinity to the target. In one embodiment, the C-5 position of the pyrimidine bases may be modified. Aptamers containing nucleotides with modified bases have a number of properties that are different than the properties of standard aptamers that include only naturally occurring nucleotides (i.e., unmodified nucleotides). In one embodiment, the method for modification of the nucleotides includes the use of an amide linkage. However, other suitable methods for modification may be used.

As used herein the term "amplification" or "amplifying" means any process or combination of process steps that increases the amount or number of copies of a molecule or class of molecules.

"SELEX target" or "target molecule" or "target" refers herein to any compound upon which a nucleic acid can act in a desirable manner. A SELEX target molecule can be a protein, peptide, nucleic acid, carbohydrate, lipid, polysaccharide, glycoprotein, hormone, receptor, antigen, antibody, virus, pathogen, toxic substance, substrate, metabolite, transition state analog, cofactor, inhibitor, drug, dye, nutrient, growth factor, cell, tissue, any portion or fragment of any of the foregoing, etc., without limitation. Further the target may be modified in one or more fashion. For example, proteins may be modified by glycosylation, phosphorylation, acetylation, phospholipids, and so forth. The target may be modified to different levels. Slow off-rate aptamers could be produced to differentiate the type or level of modification. In one embodiment, a SELEX target does not include molecules that are known to bind nucleic acids, such as, for example, known nucleic acid binding proteins (e.g. transcription factors). Virtually any chemical or biological effector may be a suitable SELEX target. Molecules of any size can serve as SELEX targets. A target can also be modified in certain ways to enhance the likelihood or strength of an interaction between the target and the nucleic acid. A target can also include any minor variation of a particular compound or molecule, such as, in the case of a protein, for example, minor variations in amino acid sequence, disulfide bond formation, glycosylation, lipidation, acetylation, phosphorylation, or any other manipulation or modification, such as conjugation with a labeling component, which does not substantially alter the identity of the molecule.

"Tissue target" or "tissue" refers to a certain subset of the SELEX targets described above. According to this definition, tissues are collections of macromolecules in a heterogeneous environment. As used herein, tissue refers to a single cell type, a collection of cell types, an aggregate of cells, or an aggregate of macromolecules. This differs from simpler SELEX targets which are typically isolated soluble molecules, such as proteins. In the one embodiment, tissues are insoluble macromolecules which are orders of magnitude larger than simpler SELEX targets. Tissues are complex targets made up of numerous macromolecules, each macromolecule having numerous epitopes that can be proteins, lipids, carbohydrates, etc., or combinations thereof. Tissues are generally a physical array of macromolecules that can be either fluid or rigid, both in terms of structure and composition. Extracellular matrix is an example of a more rigid tissue, both structurally and compositionally, while a membrane bilayer is more fluid in structure and composition. Tissues are generally not soluble and remain in solid phase, and thus partitioning can be accomplished relatively easily. Tissue includes, but is not limited to, an aggregate of cells usually of a particular kind together with their intercellular substance that form one of the structural materials commonly used to denote the general cellular fabric of a given organ, e.g., kidney tissue, brain tissue. The four general classes of tissues are epithelial tissue, connective tissue, nerve tissue, and muscle tissue.

Examples of tissues which fall within this definition include, but are not limited to, heterogeneous aggregates of macromolecules such as fibrin clots which are acellular; homgeneous or heterogeneous aggregates of cells; higher ordered structures containing cells which have a specific function, such as organs, tumors, lymph nodes, arteries, etc.; and individual cells. Tissues or cells can be in their natural environment, isolated, or in tissue culture. The tissue can be intact or modified. The modification can include numerous changes such as transformation, transfection, activation, and substructure isolation, e.g., cell membranes, cell nuclei, cell organelles, etc.

Sources of the tissue, cell or subcellular structures can be obtained from prokaryotes as well as eukaryotes. This includes human, animal, plant, bacterial, fungal and viral structures.

As used herein, "competitor molecule" and "competitor" are used interchangeably to refer to any molecule that can form a non-specific complex with a non-target molecule. In this context, non-target molecules include free aptamers, where, for example, a competitor can be used to inhibit the aptamer from binding (re-binding), non-specifically, to another non-target molecule. Competitor molecules include, but are not limited to oligonucleotides, polyanions (e.g., heparin, herring sperm DNA, salmon sperm DNA, tRNA, dextran sulfate, polydextran, abasic phosphodiester polymers, dNTPs, and pyrophosphate). In various embodiments, a combination of one or more competitor can be used.

As used herein, "non-specific complex" refers to a non-covalent association between two or more molecules other than an aptamer and its target molecule. A non-specific complex represents an interaction between classes of molecules. Non-specific complexes include complexes formed between an aptamer and a non-target molecule, a competitor and a non-target molecule, a competitor and a target molecule, and a target molecule and a non-target molecule.

As used herein, the term "slow off-rate enrichment process" refers to a process of altering the relative concentrations of certain components of a candidate mixture such that the relative concentration of aptamer affinity complexes having slow dissociation rates is increased relative to the concentration of aptamer affinity complexes having faster, less desirable dissociation rates. In one embodiment, the slow off-rate enrichment process is a solution-based slow off-rate enrichment process. In this embodiment, a solution-based slow off-rate enrichment process takes place in solution, such that neither the target nor the nucleic acids forming the aptamer affinity complexes in the mixture are immobilized on a solid support during the slow off-rate enrichment process. In various embodiments, the slow off-rate enrichment process can include one or more steps, including the addition of an incubation with a competitor molecule, dilution of the mixture, or a combination of these (e.g., dilution of the mixture in the presence of a competitor molecule). Because the effect of an slow off-rate enrichment process generally depends upon the differing dissociation rates of different aptamer affinity complexes (i.e., aptamer affinity complexes formed between the target molecule and different nucleic acids in the candidate mixture), the duration of the slow off-rate enrichment process is selected so as to retain a high proportion of aptamer affinity complexes having slow dissociation rates while substantially reducing the number of aptamer affinity complexes having fast dissociation rates. The slow off-rate enrichment process may be used in one or more cycles during the SELEX process. When dilution and the addition of a competitor are used in combination, they may be performed simultaneously or sequentially, in any order. The slow off-rate enrichment process can be used when the total target (protein) concentration in the mixture is low. In one embodiment, when the slow off-rate enrichment process includes dilution, the mixture can be diluted as much as is practical, keeping in mind that the nucleic acids are recovered for subsequent rounds in the SELEX process. In one embodiment, the slow off-rate enrichment process includes the use of a competitor as well as dilution, permitting the mixture to be diluted less than might be necessary without the use of a competitor.

In one embodiment, the slow off-rate enrichment process includes the addition of a competitor, and the competitor is a polyanion (e.g., heparin or dextran sulfate (dextran)). Heparin or dextran have been used in the identification of specific aptamers in prior SELEX selections. In such methods, however, heparin or dextran is present during the equilibration step in which the target and aptamer bind to form complexes.

In such methods, as the concentration of heparin or dextran increases, the ratio of high affinity target/aptamer complexes to low affinity target/aptamer complexes increases. However, a high concentration of heparin or dextran can reduce the number of high affinity target/aptamer complexes at equilibrium due to competition for target binding between the nucleic acid and the competitor. In other embodiments the competitor is added after the target/aptamer complexes have been allowed to form and therefore does not affect the number of complexes formed. Addition of competitor after equilibrium binding has occurred between target and aptamer creates a non-equilibrium state that evolves in time to a new equilibrium with fewer target/aptamer complexes. Trapping target/aptamer complexes before the new equilibrium has been reached enriches the sample for slow off-rate aptamers since fast off-rate complexes will dissociate first.

Thus, in one embodiment a modified SELEX process is provided for the identification or production of aptamers having slow (long) off-rates wherein the target and candidate mixture are contacted and incubated together for a period of time sufficient for equilibrium binding between the target and nucleic acids contained in the candidate mixture to occur. Following equilibrium binding an excess of competitor molecule, e.g., polyanion competitor, is added to the mixture and the mixture is incubated together with the excess of competitor molecule for a predetermined period of time. A significant proportion of aptamers having off-rates that are less than this predetermined incubation period will dissociate from the target during the predetermined incubation period. Re-association of these "fast" off-rate aptamers with the target is minimized because of the excess of competitor molecule which can non-specifically bind to the target and occupy aptamer binding sites on the target. A significant proportion of aptamers having longer off-rates will remain complexed to the target during the predetermined incubation period. At the end of the incubation period, partitioning nucleic acid-target complexes from the remainder of the mixture allows for the separation of a population of slow off-rate aptamers from those having fast off-rates. A dissociation step can be used to dissociate the slow off-rate aptamers from their target and allows for isolation, identification, sequencing, synthesis and amplification of slow off-rate aptamers (either of individual aptamers or of a group of slow off-rate aptamers) that have high affinity and specificity for the target molecule. As with conventional SELEX the aptamer sequences identified from one round of the modified SELEX process can be used in the synthesis of a new candidate mixture such that the steps of contacting, equilibrium binding, addition of competitor molecule, incubation with competitor molecule and partitioning of slow off-rate aptamers can be iterated/repeated as many times as desired.

The combination of allowing equilibrium binding of the candidate mixture with the target prior to addition of competitor, followed by the addition of an excess of competitor and incubation with the competitor for a predetermined period of time allows for the selection of a population of aptamers having off-rates that are much greater than those previously achieved.

Once a specific slow off-rate aptamer to the desired target is selected it may be produced synthetically or through cloning or any other method for producing the specific nucleic acid sequence.

Further specificity may be introduced by the process called "counter-SELEX" that effectively discards ligands that have ability to bind the target as well as closely related structural analogs of the target or targets within normal tissue or cell samples. In this embodiment, slow off-rate aptamers are selected for a specific tissue and then a counter selection is done against a related tissue which does not have certain characteristics for which the aptamer is desired. The counter selection can be done against a similar cell line or cell type, different cells, normal tissue, plasma or blood, a non-specific antibody or other available ligand. An example of this counter selection as relates to the instant disclosure would be to first select using a mixture of sperm cells as the target and then counter select the resulting nucleic acids against a similar cell type in this case a mixture of HeLa cells (a surrogate for human female epithelial cells). Aptamers that interact with both sperm cells HeLa cells will be removed by this negative selection and only those aptamers that specifically bind the sperm cells will be identified (or retained). The resulting aptamer would be specific for sperm cells. This technique will provide the ability to identify aptamers that can discriminate between two closely related targets, i.e., between a cancerous cell and an untransformed cell of the same tissue type.

To generate a slow off-rate aptamer to a cell or tissue target, the cell or tissue sample is first mixed with a candidate mixture and equilibrium binding achieved. In order to achieve equilibrium binding, the candidate mixture is incubated with the target for at least about 5 minutes, or at least about 15 minutes, about 30 minutes, about 45 minutes, about 1 hour, about 2 hours, about 3 hours, about 4 hours, about 5 hours or about 6 hours. Once equilibrium binding is achieved the selection process may proceed.

In one embodiment, a competitor is used as an off-rate enhancement process. The predetermined incubation period of competitor molecule with the mixture of the candidate mixture and target may be selected as desired, taking account of factors such as the nature of the target and known off-rates (if any) of known aptamers for the target. Predetermined incubation periods may be chosen from: at least about 5 minutes, at least about 10 minutes, at least about 20 minutes, at least about 30 minutes, at least 45 about minutes, at least about 1 hour, at least about 2 hours, at least about 3 hours, at least about 4 hours, at least about 5 hours, at least about 6 hours.

In other embodiments, a dilution is used as an off-rate enhancement process and incubation of the diluted candidate mixture, target/aptamer complex may be undertaken for a predetermined period of time, which may be chosen from: at least about 5 minutes, at least about 10 minutes, at least about 20 minutes, at least about 30 minutes, at least about 45 minutes, at least about 1 hour, at least about 2 hours, at least about 3 hours, at least about 4 hours, at least about 5 hours, at least about 6 hours.

Embodiments of the present disclosure are concerned with the identification, production, synthesis and use of slow off-rate aptamers as well as uses of any specific aptamer. These are aptamers which have a dissociation half-life ($t_{1/2}$) from a non-covalent aptamer-target complex that is higher than that of aptamers normally obtained by conventional SELEX. For a mixture containing non-covalent complexes of aptamer and target, the $t_{1/2}$ represents the time taken for half of the aptamers to dissociate from the aptamer-target complexes. The $t_{1/2}$ of slow dissociation rate aptamers according to the present disclosure is chosen from one of: greater than or equal to about 15 minutes; between about 15 minutes and about 30 minutes; between about 30 minutes and about 240 minutes; between about 30 minutes to about 60 minutes; between about 60 minutes to about 90 minutes, between about 90 minutes to about 120 minutes; between about 120 minutes to about 150 minutes; between about 150 minutes to about 180 minutes; between about 180 minutes to about 210 minutes; between about 210 minutes to about 240 minutes.

A characterizing feature of an aptamer identified by a SELEX procedure is its high affinity for its target. In some embodiments, an aptamer will have a dissociation constant ($K_d$) for its target that is chosen from one of: less than about 1 µM, less than about 100 nM, less than about 10 nM, less than about 1 nM, less than about 100 pM, less than about 10 pM, less than about 1 pM.

As used herein, the term "labeling agent," "label," or "detectable moiety," or "detectable element" or "detectable component" refers to one or more reagents that can be used to detect a target molecule/aptamer complex. A detectable moiety or label is capable of being detected directly or indirectly. In general, any reporter molecule that is detectable can be a label. Labels include, for example, (i) reporter molecules that can be detected directly by virtue of generating a signal, (ii) specific binding pair members that may be detected indirectly by subsequent binding to a cognate that contains a reporter molecule, (iii) mass tags detectable by mass spectrometry, (iv) oligonucleotide primers that can provide a template for amplification or ligation, and (v) a specific polynucleotide sequence or recognition sequence that can act as a ligand, such as, for example, a repressor protein, wherein in the latter two instances the oligonucleotide primer or repressor protein will have, or be capable of having, a reporter molecule, and so forth. The reporter molecule can be a catalyst, such as an enzyme, a polynucleotide coding for a catalyst, promoter, dye, fluorescent molecule, quantum dot, chemiluminescent molecule, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectable group, a mass tag that alters the weight of the molecule to which it is conjugated for mass spectrometry purposes, and the like. The label can be selected from electromagnetic or electrochemical materials. In one embodiment, the detectable label is a fluorescent dye. Other labels and labeling schemes will be evident to one skilled in the art based on the disclosure herein.

A detectable moiety (element or component) can include any of the reporter molecules listed above and any other chemical or component that may be used in any manner to generate a detectable signal. The detectable moiety, or signal generating label, may be detected via a fluorescent signal, a chemiluminescent signal, or any other detectable signal that is dependent upon the identity of the moiety. In the case where the detectable moiety is an enzyme (for example, alkaline phosphatase), the signal may be generated in the presence of the enzyme substrate and any additional factors necessary for enzyme activity. In the case where the detectable moiety is an enzyme substrate, the signal may be generated in the presence of the enzyme and any additional factors necessary for enzyme activity. Suitable reagent configurations for attaching the detectable moiety to a target molecule include covalent attachment of the detectable moiety to the target molecule, non-covalent association of the detectable moiety with another labeling agent component that is covalently attached to the target molecule, and covalent attachment of the detectable moiety to a labeling agent component that is non-covalently associated with the target molecule.

Detectable moieties may be incorporated into an aptamer during synthesis by using labeled dNTPs, dyes that have been generated as phosphoramidites, or other chemistries that can be employed during oligonucleotide synthesis, or may be incorporated by modification of the final aptamer product after synthesis. Each aptamer may include multiple detectable moieties to enhance signal generation. When multiple targets from the same sample, for example a histological tissue section, are to be detected then each target specific aptamer may be produced with a unique detectable moiety for simultaneous analysis of multiple targets.

In some embodiments, the labeled aptamers make possible rapid and specific staining of tissue or cell samples. For example, in some instances specific target staining of tissue sections or cell preparations may be achieved in ≤ about 15 minutes, ≤ about 10 minutes, ≤ about 5 minutes, and ≤ about 1 minute. Rapid staining is particularly advantageous in the diagnosis of abnormal or diseased tissue in an intraoperative setting.

As used herein, "partitioning" means any process whereby one or more components of a mixture are separated from other components of the mixture. For example, aptamers bound to target molecules can be partitioned from other nucleic acids that are not bound to target molecules and from non-target molecules. More broadly stated, partitioning allows for the separation of all the nucleic acids in a candidate mixture into at least two pool's based on their relative affinity and/or dissociation rate to the target molecule. Partitioning can be accomplished by various methods known in the art, including filtration, affinity chromatography, liquid-liquid partitioning, HPLC, etc. For example, nucleic acid-protein pairs can be bound to nitrocellulose filters while unbound nucleic acids are not. Columns that specifically retain nucleic acid-target complexes can also be used for partitioning. For example, oligonucleotides able to associate with a target molecule bound on a column allow the use of column chromatography for separating and isolating the highest affinity aptamers. Beads upon which target molecules are conjugated can also be used to partition aptamers in a mixture. If the beads are paramagnetic, the partitioning can be achieved through application of a magnetic field. Surface plasmon resonance technology can be used to partition nucleic acids in a mixture by immobilizing a target on a sensor chip and flowing the mixture over the chip, wherein those nucleic acids having affinity for the target can be bound to the target, and the remaining nucleic acids can be washed away. Liquid-liquid partitioning can be used as well as filtration gel retardation and density gradient centrifugation. Affinity tags on the target molecules can also be used to separate nucleic acid molecules bound to the tagged target from aptamers that are free in solution. For example, biotinylated target molecules, along with aptamers bound to them, can be sequestered from the solution of unbound nucleic acid sequences using streptavidin paramagnetic beads. Affinity tags can also be incorporated into the aptamer during preparation. When Tissue SELEX is used to produce aptamers specific to one or more targets in a biological tissue (tissue section or cell preparation), the non-specific nucleic acids in a candidate mixture may be separated from the target specific aptamers by washing the tissue sample with one or more series of buffered reagents.

As used herein, the term "the affinity SELEX process" refers to embodiments of the SELEX process in which non-photocrosslinking aptamers to targets are generated. In some embodiments of the affinity SELEX process, the target is immobilized on a solid support either before or after the target is contacted with the candidate mixture of nucleic acids. The association of the target with the solid support allows nucleic acids in the candidate mixture that have bound and in the case where a slow off-rate enrichment process is used, stay bound to the target to be partitioned from the remainder of the candidate mixture. The term "bead affinity SELEX process" refers to particular embodiments of the affinity SELEX process where the target is immobilized on a bead, for example, before contact with the candidate mixture of nucleic acids. In some embodiments, the beads are paramagnetic beads. The term "filter affinity SELEX process" refers to embodiments where nucleic acid target complexes are partitioned from candidate mixture by virtue of their association with a filter, such as a nitrocellulose filter. This includes embodiments where the target and nucleic acids are initially contacted in solution, and contacted with the filter, and also includes embodiments where nucleic acids are contacted with target that is pre-immobilized on the filter. The term "plate affinity SELEX process" refers to embodiments where the target is immobilized on the surface of a plate, such as, for example, a multi-well microtiter plate. In some embodiments, the plate is comprised of polystyrene. In some embodiments, the target is attached to the plate in the plate affinity SELEX process through hydrophobic interactions.

The present disclosure describes SELEX methods for identifying and/or producing aptamers, including slow off-rate aptamers that are capable of selectively binding to sperm cells in a sample. In one embodiment, a method is provided for identifying an aptamer having a slow rate of dissociation from its target, which in this case is sperm cells, the method comprising: preparing a candidate mixture of nucleic acid sequences; contacting the candidate mixture with a sperm cell sample wherein nucleic acids with the highest relative affinities to the target sperm cells in the sample preferentially bind to them, forming nucleic acid-sperm cell complexes; optionally applying a slow off-rate enrichment process to allow the dissociation of nucleic acid-sperm cell complexes with relatively fast dissociation rates; partitioning the remaining nucleic acid-sperm cell complexes from both free nucleic acids and non-target molecules in the candidate mixture; and identifying an aptamer to sperm cells. The process may further include the iterative step of amplifying the nucleic acids that bind to the sperm cells to yield a mixture of nucleic acids enriched in sequences that are able to bind to the sperm cells with slow dissociation rates. As defined above, the slow off-rate enrichment process can be selected from (a) diluting the candidate mixture containing the nucleic acid-sperm cell complexes; (b) adding at least one competitor to the candidate mixture containing the nucleic acid-sperm cell complexes, and diluting the candidate mixture containing the nucleic acid-sperm cell complexes; (c) and adding at least one competitor to the candidate mixture containing the nucleic acid-sperm cell complexes.

In one embodiment, a method is provided for identifying and/or producing an aptamer having a slow rate of dissociation from its sperm cell target, the method comprising: preparing a candidate mixture of nucleic acids; contacting the candidate mixture with a sperm cell containing sample, wherein nucleic acids having an increased affinity to sperm cells relative to other nucleic acids in the candidate mixture bind the sperm cells, forming nucleic acid-sperm cell target complexes; incubating the candidate mixture and sperm cells together for a period of time sufficient to achieve equilibrium binding; applying a slow off-rate enrichment process to allow the dissociation of nucleic acid-sperm cell complexes with relatively fast dissociation rates; incubating the mixture of the candidate mixture and the nucleic acid-sperm cell complexes for a predetermined period of time; partitioning the nucleic acid-sperm cell complexes from the candidate mixture; dissociating the nucleic acid-sperm cell complexes to generate free nucleic acids; amplifying the free nucleic acids to yield a mixture of nucleic acids enriched in nucleic acid sequences that are capable of binding to sperm cells with increased affinity, whereby an aptamer to sperm cells may be identified. As defined above, the slow off-rate enrichment process can be selected from (a) diluting the candidate mixture containing the nucleic acid-sperm cell complexes; (b) adding at least one competitor to the candidate mixture containing the nucleic acid-sperm cell complexes, and diluting the candidate mixture containing the nucleic acid-sperm cell complexes; (c) and adding at least one competitor to the candidate mixture containing the nucleic acid-sperm cell complexes.

In another embodiment, a method is provided for identifying and/or producing an aptamer having a slow rate of dissociation from its sperm cell target, the method comprising: preparing a candidate mixture of nucleic acids; preparing a sample by treating a sperm cell containing sample with a detergent to remove the plasma membranes from said sperm cells; contacting the candidate mixture with the sample, wherein nucleic acids having an increased affinity to sperm cells relative to other nucleic acids in the candidate mixture bind the sperm cells, forming nucleic acid-sperm cell target complexes; optionally applying a slow off-rate enrichment process to allow the dissociation of nucleic acid-sperm cell complexes with relatively fast dissociation rates; partitioning the increased affinity nucleic acids from the remainder of the candidate mixture; and identifying and/or producing an aptamer to sperm cells. The process may further include the iterative step of amplifying the nucleic acids that bind to sperm cells to yield a mixture of nucleic acids enriched in sequences that are able to bind to the sperm cells with slow dissociation rates. As defined above, the slow off-rate enrichment process can be selected from (a) diluting the candidate mixture containing the nucleic acid-sperm cell complexes; (b) adding at least one competitor to the candidate mixture containing the nucleic acid-sperm cell complexes, and diluting the candidate mixture containing the nucleic acid-sperm cell complexes; (c) and adding at least one competitor to the candidate mixture containing the nucleic acid-sperm cell complexes.

In another embodiment, a method is provided for identifying and/or producing an aptamer having a slow rate of dissociation from its sperm cell target, the method comprising: preparing a candidate mixture of nucleic acids; preparing a sample by treating a sperm cell containing sample with a detergent to remove the plasma membranes from said sperm cells; contacting the candidate mixture with the sample, wherein nucleic acids having an increased affinity to sperm cells relative to other nucleic acids in the candidate mixture bind the sperm cells, forming nucleic acid-sperm cell target complexes; optionally applying a slow off-rate enrichment process to allow the dissociation of nucleic acid-sperm cell complexes with relatively fast dissociation rates; partitioning the increased affinity nucleic acids from the remainder of the candidate mixture; contacting the increased nucleic acid-sperm cell complexes with one or more non-target molecules, wherein nucleic acids with affinity to the non-target molecule(s) are removed; and identifying and/or producing an aptamer to sperm cells. The process may further include the iterative step of amplifying the nucleic acids that bind to sperm cells to yield a mixture of nucleic acids enriched in sequences that are able to bind to the sperm cells with slow dissociation rates. As defined above, the slow off-rate enrichment process can be selected from (a) diluting the candidate mixture containing the nucleic acid-sperm cell complexes; (b) adding at least one competitor to the candidate mixture containing the nucleic acid-sperm cell complexes, and diluting the candidate mixture containing the nucleic acid-sperm cell complexes; (c) and adding at least one competitor to the candidate mixture containing the nucleic acid-sperm cell complexes.

In another embodiment, a method is provided for identifying and/or producing an aptamer having a slow rate of dissociation from sperm cells, the method comprising: preparing a candidate mixture of nucleic acids, wherein the candidate mixture comprises modified nucleic acids in which one, several or all pyrimidines in at least one, or each, nucleic acid of the candidate mixture is chemically modified at the 5-position; contacting the candidate mixture with a sperm cell sample, wherein nucleic acids having an increased affinity to sperm cells relative to other nucleic acids in the candidate mixture bind the sperm cells, forming nucleic acid-sperm cell complexes; optionally applying a slow off-rate enrichment process to allow the dissociation of nucleic acid-sperm cell complexes with relatively fast dissociation rates; partitioning the increased affinity nucleic acids from the remainder of the candidate mixture; and identifying and/or producing an aptamer to sperm cells. The process may further include the iterative step of amplifying the nucleic acids that bind to sperm cells to yield a mixture of nucleic acids enriched in sequences that are able to bind to the sperm cells with slow dissociation rates. As defined above, the slow off-rate enrichment process can be selected from (a) diluting the candidate mixture containing the nucleic acid-sperm cell complexes; (b) adding at least one competitor to the candidate mixture containing the nucleic acid-sperm cell complexes, and diluting the candidate mixture containing the nucleic acid-sperm cell complexes; (c) and adding at least one competitor to the candidate mixture containing the nucleic acid-sperm cell complexes.

In yet another embodiment, a method is provided for identifying and/or producing an aptamer having a slow rate of dissociation from sperm cells, the method comprising: preparing a candidate mixture of nucleic acids, wherein the candidate mixture comprises modified nucleic acids in which one, several or all pyrimidines in at least one, or each, nucleic acid of the candidate mixture is chemically modified at the 5-position; preparing a sample by treating a sperm cell containing sample with a detergent to remove the plasma membranes from said sperm cells; contacting the candidate mixture with the sample, wherein nucleic acids having an increased affinity to sperm cells relative to other nucleic acids in the candidate mixture bind the sperm cells, forming nucleic acid-sperm cell complexes; optionally applying a slow off-rate enrichment process to allow the dissociation of nucleic acid-sperm cell complexes with relatively fast dissociation rates; partitioning the increased affinity nucleic acids from the remainder of the candidate mixture; and identifying and/or producing an aptamer to sperm cells. The process may further include the iterative step of amplifying the nucleic acids that bind to sperm cells to yield a mixture of nucleic acids enriched in sequences that are able to bind to the sperm cells with slow dissociation rates. As defined above, the slow off-rate enrichment process can be selected from (a) diluting the candidate mixture containing the nucleic acid-sperm cell complexes; (b) adding at least one competitor to the candidate mixture containing the nucleic acid-sperm cell complexes, and diluting the candidate mixture containing the nucleic acid-sperm cell complexes; (c) and adding at least one competitor to the candidate mixture containing the nucleic acid-sperm cell complexes.

In yet another embodiment, a method is provided for identifying and/or producing an aptamer having a slow rate of dissociation from sperm cells, the method comprising: preparing a candidate mixture of nucleic acids, wherein the candidate mixture comprises modified nucleic acids in which one, several or all pyrimidiries in at least one, or each, nucleic acid of the candidate mixture is chemically modified at the 5-position; preparing a sample by treating a sperm cell containing sample with a detergent to remove the plasma membranes from said sperm cells; contacting the candidate mixture with the sample, wherein nucleic acids having an increased affinity to sperm cells relative to other nucleic acids in the candidate mixture bind the sperm cells, forming nucleic acid-sperm cell complexes; optionally applying a slow off-rate enrichment process to allow the dissociation of nucleic acid-sperm cell complexes with relatively fast dissociation rates; partitioning the increased affinity nucleic acids from the remainder of the candidate mixture; contacting the increased nucleic acid-sperm cell complexes with one or more non-target molecules, wherein nucleic acids with affinity to the non-target molecule(s) are removed; and identifying and/or producing an aptamer to sperm cells. The process may further include the iterative step of amplifying the nucleic acids that bind to sperm cells to yield a mixture of nucleic acids enriched in sequences that are able to bind to the sperm cells with slow dissociation rates. As defined above, the slow off-rate enrichment process can be selected from (a) diluting the candidate mixture containing the nucleic acid-sperm cell complexes; (b) adding at least one competitor to the candidate mixture containing the nucleic acid-sperm cell complexes, and diluting the candidate mixture containing the nucleic acid-sperm cell complexes; (c) and adding at least one competitor to the candidate mixture containing the nucleic acid-sperm cell complexes.

In another embodiment, a method is provided for identifying and/or producing an aptamer having a slow rate of dissociation from sperm cells, the method comprising preparing a candidate mixture of nucleic acid sequences; contacting the candidate mixture with a sperm cell sample wherein nucleic acids with the highest relative affinities to the target sperm cells in the sample preferentially bind to them, forming nucleic acid-sperm cell complexes; applying a slow off-rate enrichment process to allow the dissociation of nucleic acid-sperm cell complexes with relatively fast dissociation rates; partitioning the nucleic acid-sperm cell complexes from the candidate mixture; contacting the nucleic acid-sperm cell complexes with one or more non-target molecules, wherein nucleic acids with affinity to the non-target molecule(s) are removed; and identifying and/or producing an aptamer to sperm cells. The process may further include the iterative step of amplifying the nucleic acids that bind to the sperm cells to yield a mixture of nucleic acids enriched in sequences that are able to bind to the sperm cells with slow dissociation rates. As defined above, the slow off-rate enrichment process can be selected from (a) diluting the candidate mixture containing the nucleic acid-sperm cell complexes; (b) adding at least one competitor to the candidate mixture containing the nucleic acid-sperm cell complexes, and diluting the candidate mixture containing the nucleic acid-sperm cell complexes; (c) and adding at least one competitor to the candidate mixture containing the nucleic acid-sperm cell complexes.

In one embodiment, a method is provided for identifying and/or producing an aptamer having a slow rate of dissociation from its sperm cell target, the method comprising: preparing a candidate mixture of nucleic acids; contacting the candidate mixture with a sperm cell containing sample, wherein nucleic acids having an increased affinity to sperm cells relative to other nucleic acids in the candidate mixture bind the sperm cells, forming nucleic acid-sperm cell target complexes; incubating the candidate mixture and sperm cells together for a period of time sufficient to achieve equilibrium binding; applying a slow off-rate enrichment process to allow the dissociation of nucleic acid-sperm cell complexes with relatively fast dissociation rates to the mixture; incubating the mixture of the candidate mixture and the nucleic acid-sperm cell complexes for a predetermined period of time; partitioning the nucleic acid-sperm cell complexes from the candidate mixture; contacting the increased nucleic acid-sperm cell complexes with one or more non-target molecules, wherein nucleic acids with affinity to the non-target molecule(s) are removed; dissociating the nucleic acid-sperm cell complexes to generate free nucleic acids; amplifying the free nucleic acids to yield a mixture of nucleic acids enriched in nucleic acid sequences that are capable of binding to sperm cells with increased affinity, whereby an aptamer to sperm cells may be identified. As defined above, the slow off-rate enrichment process can be selected from (a) diluting the candidate mixture containing the nucleic acid-sperm cell complexes; (b) adding at least one competitor to the candidate mixture containing the nucleic acid-sperm cell complexes, and diluting the candidate mixture containing the nucleic acid-sperm cell complexes; (c) and adding at least one competitor to the candidate mixture containing the nucleic acid-sperm cell complexes.

In another embodiment, a method is provided for identifying and/or producing an aptamer having a slow rate of dissociation from sperm cells, the method comprising: preparing a candidate mixture of nucleic acids, wherein the candidate mixture comprises modified nucleic acids in which one, several or all pyrimidines in at least one, or each, nucleic acid of the candidate mixture is chemically modified at the 5-position; contacting the candidate mixture with a sperm cell sample, wherein nucleic acids having an increased affinity to sperm cells relative to other nucleic acids in the candidate mixture bind the sperm cells, forming nucleic acid-sperm cell complexes; partitioning the increased affinity nucleic acids from the remainder of the candidate mixture; contacting the increased nucleic acid-sperm cell complexes with one or more non-target molecules, wherein nucleic acids with affinity to the non-target molecule(s) are removed, and identifying and/or producing an aptamer to sperm cells. The process may further include the iterative step of amplifying the nucleic acids that bind to the sperm cells to yield a mixture of nucleic acids enriched in sequences that are able to bind to the sperm cells with slow dissociation rates. As defined above, the slow off-rate enrichment process can be selected from (a) diluting the candidate mixture containing the nucleic acid-sperm cell complexes; (b) adding at least one competitor to the candidate mixture containing the nucleic acid-sperm cell complexes, and diluting the candidate mixture containing the nucleic acid-sperm cell complexes; (c) and adding at least one competitor to the candidate mixture containing the nucleic acid-sperm cell complexes.

In another embodiment, a non-covalent complex of an aptamer and its sperm cell target is provided, wherein the dissociation half-life ($t_{1/2}$) of the aptamer from the sperm cell target is chosen from one of: greater than or equal to about 15 minutes; between about 15 minutes and about 30 minutes; between about 30 minutes and about 240 minutes; about 30 minutes to about 60 minutes; about 60 minutes to about 90 minutes; about 90 minutes to about 120 minutes; about 120 minutes to about 150 minutes; about 150 minutes to about 180 minutes; about 180 minutes to about 210 minutes; about 210 minutes to about 240 minutes.

In another embodiment, a non-covalent complex of an aptamer and a sperm cell is provided, wherein the aptamer has a $K_d$ for the target of about 100 nM or less, wherein the dissociation half-life ($t_{1/2}$) of the aptamer from the target is greater than or equal to about 15 minutes, and wherein one, several or all pyrimidines in the nucleic acid sequence of the aptamer are modified at the 5-position of the base. The modifications may be selected from the group of compounds shown in FIG. 1, these modifications are referred to as "base modified nucleotides". Aptamers may be designed with any combination of the base modified pyrimidines desired.

Diagnostic or assay devices, e.g. columns, test strips or biochips, having one or more slow off-rate aptamers adhered to a solid surface of the device are also provided. The aptamer(s) may be positioned so as to be capable of binding target molecules that are contacted with the solid surface to form aptamer-target complexes that remain adhered to the surface of the device, thereby capturing the target and enabling detection, quantitation or subsequent genetic characterization of the target. An array of slow off-rate aptamers (which may be the same or different) may be provided on such a device.

As used herein "binding" generally refers to the formation of a non-covalent association between the ligand and the target, although such binding is not necessarily reversible. The terms "nucleic acid-target complex" or "complex" or "affinity complex" are used to refer to the product of such non-covalent binding association.

In various embodiments, aptamers, including slow off-rate aptamers can be single- or double-stranded RNA or DNA oligonucleotides. The aptamers can contain non-standard or modified bases. Further, the aptamers can contain any type of modification. As used herein, a "modified base" may include a relatively simple modification to a natural nucleic acid residue, which modification confers a change in the physical properties of the nucleic acid residue. Such modifications include, but are not limited to, modifications at the 5-position of pyrimidines, substitution with hydrophobic groups, e.g., benzyl, iso-butyl, indole, or napthylmethyl, or substitution with hydrophilic groups, e.g., quaternary amine or guanidinium, or more "neutral" groups, e.g., imidazole and the like. Additional modifications may be present in the ribose ring, e.g., 2'-position, such as 2'-amino (2'-$NH_2$) and 2'-fluoro (2'-F), or the phosphodiester backbone, e.g., phosphorothioates or methyl phosphonates.

In another embodiment, an aptamer that includes a cleavable or releasable section in the fixed region of the aptamer is produced. The aptamer can also be produced with one or more of the following additional components: a labeled component, a spacer component, and a specific binding tag. Any or all of these elements may be introduced into a single stranded aptamer. In one embodiment, the element is introduced at the 5' end of the aptamer. In another embodiment, one or more of these elements is included by creating a partially double stranded aptamer, where one strand contains the various elements desired as well as a sequence complementary to one of the fixed sequence sections of the second strand containing the variable target binding region.

A "releasable" or "cleavable" element or moiety or component refers to a functional group where certain bonds in the functional group can be broken to produce 2 separate components. In various embodiments, the functional group can be cleaved by irradiating the functional group (photocleavable) at the appropriate wavelength or by treatment with the appropriate chemical or enzymatic reagents. In another embodiment, the releasable element may be a disulfide bond that can be treated with a reducing agent to disrupt the bond. The releasable element allows an aptamer/target affinity complex that is attached to a solid support to be separated from the solid support, such as by elution of the complex. The releasable element may be stable to the conditions of the rest of the assay and may be releasable under conditions that will not disrupt the aptamer/target complex.

As disclosed herein, an aptamer can further comprise a "tag" or "immobilization component or element" or "specific binding component or element" which refers to a component that provides a means for attaching or immobilizing an aptamer (and any target molecule that is bound to it) to a solid support. A "tag" is a component that is capable of associating with a probe. The tag can be attached to or included in the aptamer by any suitable method. Generally, the tag allows the aptamer to associate, either directly or indirectly, with a probe or receptor that is attached to the solid support. The probe may be highly specific in its interaction with the tag and retain that association during all subsequent processing steps or procedures. A tag can enable the localization of an aptamer affinity complex (or optional covalent aptamer affinity complex) to a spatially defined address on a solid support. Different tags, therefore, can enable the localization of different aptamer covalent complexes to different spatially defined addresses on a solid support. A tag can be a polynucleotide, a polypeptide, a peptide nucleic acid, a locked nucleic acid, an oligosaccharide, a polysaccharide, an antibody, an affybody, an antibody mimic, a cell receptor, a ligand, a lipid, biotin, any fragment or derivative of these structures, any combination of the foregoing, or any other structure with which a probe (or linker molecule, as described below) can be designed or configured to bind or otherwise associate with specificity. Generally, a tag is configured such that it does not interact intramolecularly with either itself or the aptamer to which it is attached or of which it is a part. If SELEX is used to identify an aptamer, the tag may be added to the aptamer either pre- or post-SELEX. The tag is included on the 5'-end of the aptamer post-SELEX, or the tag is included on the 3'-end of the aptamer post-SELEX, or the tags may be included on both the 3' and 5' ends of the aptamers in a post-SELEX process. All constructs can be synthesized using standard phosphoramidite chemistry. The functionality can be split between the 5' and 3' end or combined on either end. In addition to photocleavable moieties, other cleavable moieties can be used, including chemically or enzymatically cleavable moieties. A variety of spacer moieties can be used and one or more biotin moieties can be included. Tags (also referred to as immobilization or specific binding elements or components) other than biotin can also be incorporated. Suitable construction reagents include biotin phosphoramidite, PC Linker (Glen Research PN 10-4920-02); PC biotin phosphoramidite (Glen Research PN 10-4950-02); dSpacer CE phosphoramidite (Glen Research PN 10-1914-02); Cy3 phosphoramidite (Glen Research PN 10-5913-02); and Arm26-Ach Spacer Amidite (Fidelity Systems PN SP26Ach-05). This type of tag on a target specific slow off-rate aptamer may be used to introduce secondary reagents, such as a label, into a tissue or cell sample. For example if the slow off-rate aptamer contains a biotin tag, a labeled avidin molecule could be introduced to generate signal.

In some embodiments, amplification occurs after members of the test mixture have been partitioned, and it is the nucleic acid that is amplified. For example, amplifying RNA molecules can be carried out by a sequence of three reactions: making cDNA copies of selected RNAs, using the polymerase chain reaction to increase the copy number of each cDNA, and transcribing the cDNA copies to obtain RNA molecules having the same sequences as the selected RNAs. Any reaction or combination of reactions known in the art can be used as appropriate, including direct DNA replication, direct RNA amplification and the like, as will be recognized by those skilled in the art. The amplification method may result in the proportions of the amplified mixture being representative of the proportions of different sequences in the mixture prior to amplification. It is known that many modifications to nucleic acids are compatible with enzymatic amplification. Modifications that are not compatible with amplification can be made after each round of amplification, if necessary.

The present disclosure includes methods for purifying sperm cells in a sample. In one embodiment, the present disclosure generally describes methods for detecting the presence of sperm cells in a sample comprising contacting said sample with an aptamer (or photoaptamer) that binds to sperm cells, thereby forming aptamer-sperm cell affinity complexes; partitioning the aptamer-sperm cell affinity complexes from the remainder of the sample and detecting and/or quantifying the presence of said sperm cells. In another embodiment, the method comprises contacting an aptamer having specific affinity for sperm cells thereby forming aptamer-sperm cell affinity complexes; optionally introducing a slow off-rate enrichment process; partitioning bound nucleic acid-sperm cell complexes from the remainder of the sample and quantifying and/or genetically characterizing said sperm cells by standard methods.

In another embodiment, an aptamer comprising a tag that has a specific affinity for sperm cells is immobilized on a solid support in solution prior to equilibration with the sample. The attachment of the aptamer to the solid support is accomplished by contacting the solid support with the aptamer and allowing the tag included on the aptamer to associate, either directly or indirectly, with an appropriate capture agent that is attached to the solid support. In some embodiments, the method further comprising washing with a solution buffered to pH 11 to remove aptamer/aptamer aggregates, thereby reducing assay background.

In one embodiment the tag is biotin and the solid support is streptavidin beads. Other possible tag/support combinations include, but are not limited to hexahistidine (tag) and nickel or cobalt-nitrilotriacetic acid-substituted magnetic beads (support). A tag may also be selected from a primary amine appended to the aptamer; which would support covalent binding to commonly available supports, e.g. carboxyl-substituted magnetic beads. Other tags include, but are not limited to a dye, a hapten, a digoxigenin; the solid supports can be selected from solid support modified with an appropriate capture agent for the respective tag.

A sample is then prepared and contacted with the immobilized aptamers that have a specific affinity for sperm cells. If the sample contains sperm cells, an aptamer-sperm cell affinity complex will form in the mixture with the sample. A slow off-rate enrichment process is optionally introduced to induce the dissociation of nucleic acid-target complexes with relatively fast dissociation rates. The aptamer-sperm cell affinity complex and uncomplexed aptamer that has associated with the probe on the solid support is then partitioned from the remainder of the mixture, thereby removing all uncomplexed matter in the sample (sample matrix); i.e., components of the mixture not associated with the solid support. Following partitioning, the sperm cells are released from the aptamer thereby allowing detection and/or quantification.

In one embodiment, the sperm cells are quantified by lysing the sperm cells and measuring the amount of DNA in the lysate. The sperm cells can also be quantified using a cytometer or any other methods that would be known to those skilled in the art.

In one embodiment the sample is prepared by stripping the sperm cells of their plasma membrane prior to contacting with the aptamer. This method comprises treating said sample with a buffered detergent prior to performing the affinity based assay. In one embodiment the detergent is selected from an anionic detergent. In one embodiment the anionic detergent is selected from the group including, but not limited Triton X-200, sodium deoxycholate, lithium dodecyl sulfate (LDS) and sodium dodecyl sulfate (SDS). In one embodiment, the detergent is an anionic detergent. In some aspects, the detergent is selected from the group including, but not limited to Triton X-200, sodium deoxycholate and lithium dodecyl sulfate (LDS). In one embodiment, the swab is selected from the group including, but not limited to a Dacron swab, a flocked nylon swab and a cotton swab.

The present disclosure further describes methods for the isolation and purification of sperm cells from solution, comprising immobilizing an aptamer that has a specific affinity for sperm cells comprising a tag that enables immobilization on a solid support in solution, contacting said aptamer with the sperm dell solution; wherein an aptamer-sperm cell affinity complex is formed; partitioning said aptamer-sperm cell affinity complex from the remainder of the solution; and releasing said sperm cell from the support bound aptamer. In some embodiments, the bound sperm cells are lysed allowing analysis of the DNA in the lysate In another embodiment the instant disclosure provides a method for the isolation and purification of sperm cells from a solution, comprising immobilizing an aptamer that has a specific affinity for sperm cells comprising a tag that enables immobilization on a solid support in solution, preparing a solution by treating a sperm cell sample with a detergent; contacting said aptamer with the test solution; wherein an aptamer-sperm cell affinity complex is formed; partitioning said aptamer-sperm cell affinity complex from the remainder of the solution; and releasing said purified sperm cells from the support bound aptamer. In some embodiments, the bound sperm cells are lysed allowing analysis of the DNA in the lysate.

The present disclosure further describes methods for the detecting, isolating or purifying sperm cells from samples eluted from a swab said method comprising: contacting said swab containing a sample with a buffered detergent solution; thereby forming a test solution containing said sample; contacting said test solution with an aptamer solution comprising a tag that has a specific affinity for sperm cells immobilized on a solid support; thereby forming an aptamer-sperm cell affinity complex; optionally introducing a slow off-rate enrichment process; partitioning the aptamer-sperm cell affinity complexes from the remainder of the test solution and detecting, purifying and/or quantifying the presence of said sperm cells. In some aspects, the aptamer comprises a detectable moiety.

The present disclosure further describes methods for identifying and producing aptamers to sperm cells. In some embodiments, the methods utilize the modified SELEX process for generating slow off-rate (slow rate of dissociation) aptamers. In one embodiment, the method comprises preparing sperm cells by detergent treatment, thereby exposing insoluble proteins of the nucleus and cytoskeleton of the sperm cells; preparing a candidate mixture of nucleic acids; contacting the candidate mixture with a prepared sperm cell sample wherein nucleic acids with the highest relative affinities to the target prepared sperm cells preferentially bind the sperm cells, forming nucleic acid-sperm cell complexes; optionally introducing a slow off-rate enrichment process to induce the dissociation of nucleic acid-sperm cell complexes with relatively fast dissociation rates; partitioning the remaining bound nucleic acid-sperm cell complexes from free nucleic acids in the candidate mixture; and identifying and/or producing the nucleic acids that were bound to the sperm cells. The process may further include the iterative step of amplifying the nucleic acids that bind to the target to yield a mixture of nucleic acids enriched with nucleic acids that bind to the target molecule yet produce nucleic acid-target molecule complexes having slow dissociation rates.

In another embodiment, the candidate mixture of nucleic acids includes nucleic acids containing modified nucleotide bases that may aid in the formation of modified nucleic acid-target complexes having slow dissociation rates.

In yet another embodiment, an extension of the SELEX process for identifying aptamers and slow off-rate aptamers, termed counter-SELEX is employed. Counter-SELEX is a method for improving the specificity of nucleic acid ligands to a target molecule by eliminating nucleic acid ligand sequences with cross-affinity to one or more non-target molecules.

In one embodiment, the aptamers are produced with a detectable moiety and may be directly detected after binding with their respective target or targets following an optional wash step to remove unreacted aptamer. In other embodiments, the one or more slow off-rate aptamers interaction with their respective target or targets is detected after the two components of an element to support signal generation are reacted.

The disclosure includes slow off-rate aptamers identified and produced according to said methods, including but not limited to the aptamers set forth in Table 2 (SEQ ID NOS: 3-5).

In yet another embodiment, the present disclosure describes the isolation of sperm from a mixture of sperm and HeLa cells, which serve as a surrogate for human female epithelial cells.

The methods of the of the instant disclosure enable rapid and facile separation of spermatozoa from female epithelial cells in mixed sexual assault evidence, and supports amplification and analysis of male DNA. The technology is intended to be cost-effective, high-throughput, commercially viable, and be easily implemented in forensic laboratories.

In one embodiment, kits using aptamer reagents can be prepared based on the methods disclosed herein.

As noted above, in some embodiments, once the slow off-rate aptamer(s) is allowed to equilibrate with the sample to form a slow off-rate aptamer target affinity complex, a kinetic challenge may be used. If a kinetic challenge is introduced, non-specific complexes between the slow off-rate aptamer and any non-target molecules are unlikely to re-form following their dissociation. Since non-specific complexes generally dissociate more rapidly than a slow off-rate aptamer affinity complex, a kinetic challenge reduces the likelihood that a slow off-rate aptamer will be involved in a non-specific complex with a non-target. An effective kinetic challenge can provide the assay with additional specificity, beyond that of the initial slow off-rate aptamer binding event and any subsequent optional covalent interaction. Thus, the kinetic challenge offers a second determinant of specificity. In one embodiment, 10 mM dextran sulfate is added to the slow off-rate aptamer affinity complexes that are tissue or cell associated, and is incubated for about 15 minutes. In another embodiment, the kinetic challenge is initiated in the presence of 10 mM dextran sulfate. In the case of a kinetic challenge that uses a competitor, the competitor can also be any molecule that can form a non-specific complex with a free slow off-rate aptamer, for example to prevent that slow off-rate aptamer from rebinding non-specifically to a non-target molecule. Such competitor molecules include polycations (e.g., spermine, spermidine, polylysine, and polyarginine) and amino acids (e.g., arginine and lysine). When a competitor is used as the kinetic challenge a fairly high concentration is utilized relative to the anticipated concentration of total protein or total slow off-rate aptamer present in the sample. In one embodiment, about 10 mM dextran sulfate is used as the competitor in a kinetic challenge. In one embodiment, the kinetic challenge comprises adding a competitor to the tissue or cell sample containing the slow off-rate aptamer affinity complex, and incubating the sample for a time of greater than or equal to about 30 seconds, about 1 minute, about 2 minutes, about 3 minutes, about 4 minutes, about 5 minutes, about 10 minutes, about 30 minutes, and about 60 minutes. In another embodiment, the kinetic challenge comprises adding a competitor to the tissue or cell sample containing the slow off-rate aptamer affinity complex and incubating for a time such that the ratio of the measured level of slow off-rate aptamer affinity complex to the measured level of the non-specific complex is increased.

In some embodiments, the kinetic challenge is performed by contacting the sample with binding buffer or any other solution that does not significantly increase the natural rate of dissociation of slow off-rate aptamer affinity complexes. The dilution can be about 2×, about 3×, about 4×, about 5×, or any suitable greater dilution. Larger dilutions provide a more effective kinetic challenge by reducing the concentration of total protein and slow off-rate aptamer after dilution and, therefore, the rate of their re-association. In one embodiment, the slow off-rate aptamer affinity complex is effectively diluted by addition of the diluent and incubated for a time about ≥30 seconds, ≥ about 1 minute, ≥ about 2 minutes, ≥ about 3 minutes, ≥ about 4 minutes, ≥ about 5 minutes, ≥ about 10 minutes, ≥ about 30 minutes, and ≥ about 60 minutes. In another embodiment, the slow off-rate aptamer affinity complex is effectively diluted by addition of a diluent and incubated for a time such that the ratio of the measured level of slow off-rate aptamer affinity complex to the measured level of the non-specific complex is increased.

In some embodiments, the kinetic challenge is performed in such a manner that the effect of sample dilution and the effect of introducing a competitor are realized simultaneously. For example, a tissue or cell sample can be effectively diluted by addition of a large volume of competitor. Combining these two kinetic challenge strategies may provide a more effective kinetic challenge than can be achieved using one strategy. In one embodiment, the effective dilution can be about 2×, about 3×, about 4×, about 5×, or any suitable greater dilution and the competitor is about 10 mM dextran sulfate. In one embodiment, the competitor is about 1 mM dextran sulfate. In one embodiment, the kinetic challenge comprises contacting the tissue or cell sample containing the slow off-rate aptamer affinity complex with a volume of diluent, adding a competitor to the mixture containing the slow off-rate aptamer affinity complex, and incubating the mixture containing the slow off-rate aptamer affinity complex for a time greater than or equal to about 30 seconds, about 1 minute, about 2 minutes, about 3 minutes, about 4 minutes, about 5 minutes, about 10 minutes, about 30 minutes, and about 60 minutes. In another embodiment, the kinetic challenge comprises diluting the mixture containing the slow off-rate aptamer affinity complex, adding a competitor to the mixture containing the slow off-rate aptamer affinity complex and incubating the mixture containing the slow off-rate aptamer affinity complex for a time such that the ratio of the measured level of slow off-rate aptamer affinity complex to the measured level of the non-specific complex is increased.

In another embodiment, the detectable moiety introduced to the sample through the binding of the aptamer may be a fluorescent, chemiluminescent, or colorimetric detectable moiety that is directly attached to the slow off-rate aptamer. When more than one aptamer is used in the buffered aptamer solution, each aptamer may include a detectable moiety with an unique wavelength of detection and/or excitation. Thus multiple targets may be detected simultaneously. Optionally these aptamers may be designed to crosslink to their specific target.

In another embodiment, the aptamer may be designed with an element to support signal generation. In one embodiment, the element to support signal generation may be an enzyme attached to the slow off-rate aptamer, or attached via a tag, such, that it does not interfere with binding of the slow off-rate aptamer to the target. Once the slow off-rate aptamer has bound to the specific target and excess slow off-rate aptamer, or slow off-rate aptamers, has been removed, the enzyme may be reacted with its specific substrate to produce a detectable signal at the site where the enzyme may be immobilized. A precipitating, colorimetric or fluorescent substrate may be used. In another embodiment, the enzyme attached to the aptamer may be used to increase the signal. In another embodiment, the element to support signal generation consists of two components. The first component of the element to support signal generation is designed into the aptamer and is ligand like biotin that reacts with a corresponding receptor like avidin, the second component of the element to support signal generation. The second component may be attached to the detectable moiety.

A reaction or buffered solution could independently contain 0.005 to 40 nM of an aptamer having specificity for sperm cells. For example, the aptamer concentration could be ≤ any of the following concentrations; 0.005 nM, 1 nM, 2 nM, 4 nM, 8 nM, 16 nM, 32 nM, 35 nM, or 40 nM by aptamer in the mix. The reaction solution could contain a buffer such SB17 (40 mM HEPES, pH 7.5, 125 mM NaCl, 5 mM KCl, 5 mM $MgCl_2$, 1 mM EDTA, 0.05% TWEEN-20) or other buffer selected empirically to minimize the changes in cells or tissues or promote aptamer diffusion into the section (tissue or cell), or to support recovery of cells from other material. The reaction solution may further contain materials to minimize non-specific binding of the aptamer to sample derived nucleic acids including for example herring sperm DNA, etc. Additional components could include dextran sulfate, a carrier protein like casein, etc. An optional kinetic challenge step could be utilized.

In another embodiment, a histological or cytological reagent is provided that may consist of one or more slow off-rate aptamers specific sperm cells In addition to the slow off-rate aptamers, the reagent may consist of buffers, salts, detergents, blocking reagents, competitors, and stabilizers.

Another aspect of the present disclosure relates to kits useful for conveniently performing any of the methods disclosed herein to analyze samples. To enhance the versatility of the disclosed methods, the reagents can be provided in packaged combination, in the same or separate containers, so that the ratio of the reagents provides for substantial optimization of the method and assay. The reagents may each be in separate containers or various reagents can be combined in one or more containers depending upon the cross-reactivity and stability of the reagents.

A kit comprises, in packaged combination, at least one aptamer. The kit may also include washing solutions such as buffered aqueous medium for sample dilution as well as slide washing, sample preparation reagents, and so forth. In addition the kit may contain reagents suitable for performing the desired kinetic challenge during the analytical method. The relative amounts of the various reagents in the kits can be varied widely to provide for concentrations of the reagents that substantially optimize the reactions that need to occur during the assay and to further substantially optimize the sensitivity of the assay. Under appropriate circumstances, one or more of the reagents in the kit can be provided as a dry powder, usually lyophilized, including excipients, which upon dissolution will provide a reagent solution having the appropriate concentrations for performing a method or assay in accordance with the present disclosure. The kit can further include a written description of a method in accordance with any of the methods as described herein.

In one embodiment, a kit for the detection and/or purification of sperm cells that may be present in a sample includes at least one aptamer having specific affinity for sperm cells.

In another embodiment, a kit for the detection and/or quantification of sperm cells that may be present in a sample includes at least one aptamer having specific affinity for a target that has a covalently attached a detection moiety/label, and at least one polyanionic competitor to reduce non-specific binding.

In addition, any of the above-described kits may contain reagents and materials for the performance of a kinetic challenge during the detection method of the kit.

Illustrative methods of the instant disclosure are described in Examples 1 and 2. Specifically, Examples 1 and 2 illustrate the generation of slow off-rate aptamers to sperm cells using the aptamer-based capture system described herein. With reference to the Examples, aptamers that specifically recognize human sperm were identified and produced using the whole cell tissue SELEX process which is illustrated schematically in FIG. 3. The selection was performed with a counter-selection step to ensure that selected aptamers would have little or no affinity for contaminating epithelial cells from forensic samples. HeLa cells were used, with the expectation that their origin (a human cervical cancer cell line) made them a reasonable surrogate for the epithelial cells that would be encountered in forensic samples.

In Vitro Selection of Aptamer Capture Reagents

In an alternate procedure, used to target highly conserved and stable proteins that would remain after elution from swabs, the sperm cells were stripped of their plasma membranes with detergent prior to selection of high affinity aptamers as described in Example 2. This treatment exposes the so-called "perinuclear calyx," which is the cytoskeletal structure that remains intact even after differential extraction. In doing so, advantage was taken of the unique opportunity afforded by in vitro selection to tailor selection conditions to satisfy the demands of the anticipated application as well as selection itself. Salt (NaCl) concentration was set at 350 mM—a condition that was expected to support efficient elution from cotton swabs as well as minimize the relatively high non-specific DNA binding observed for detergent-stripped sperm (data not shown). Chelators EDTA and EGTA were included in the selection buffer to remove divalent cations in order to suppress proteolytic and deoxynucleolytic activities that might degrade DNA or protein epitopes over a prolonged elution period. Large quantities of competitor DNA and tRNA were included, both to minimize non-specific library binding and to ensure that selected aptamers would perform in the presence of large amounts of contaminating epithelial DNA that might be expected in forensic samples. A relatively high concentration of the non-ionic detergent Triton X-100 was included to potentiate swab elution as well as support aptamer binding.

Selection progress was monitored via Cot curves of aptamer pools. Cot curves measure the complexity of a DNA sequence population. The extent and rapid rise in signal in Cot curves after rounds 5 and 6 were indicative of a relatively small population of sequence species, indicating a successful selection of a small number aptamers from the vast number of sequences represented in the original library. Seven rounds of selection in total were performed.

Figure 4A:
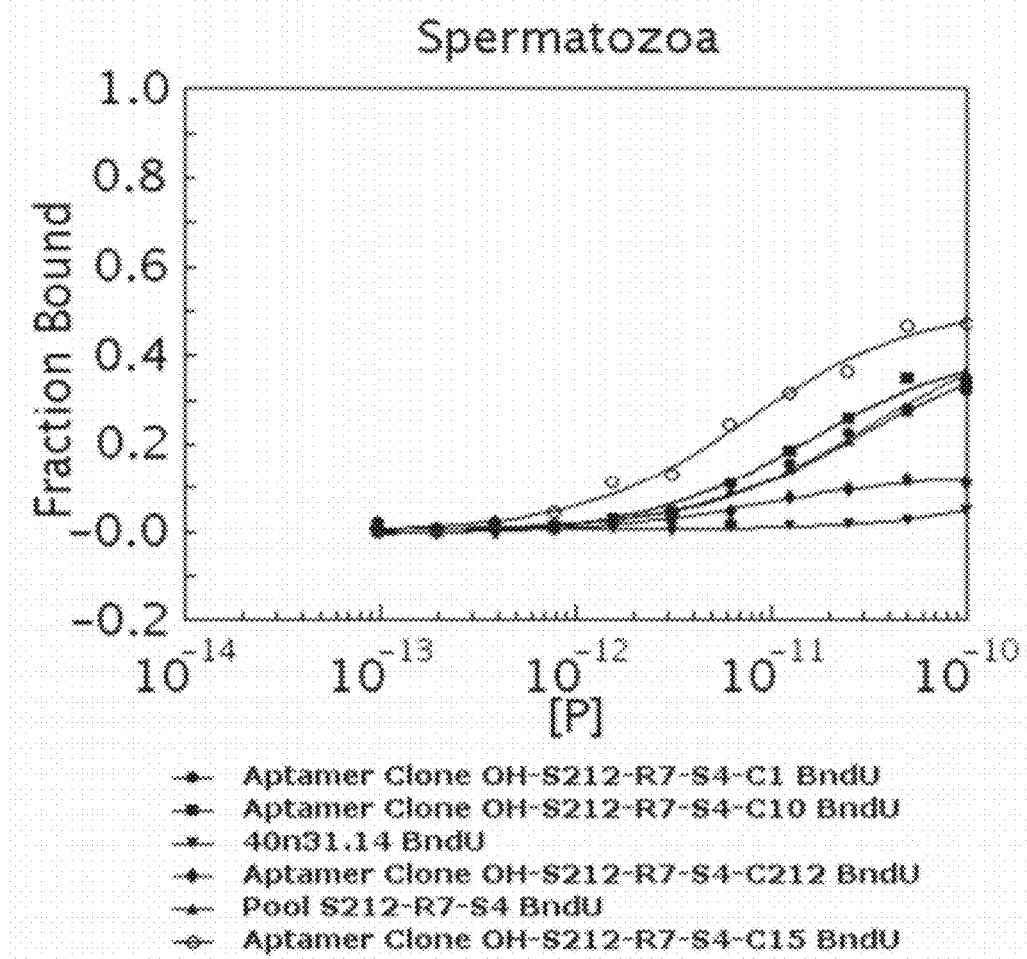
FIGS. 4A-D depict aptamer affinity characterization. Selected aptamers were characterized for their affinity and specificity to intact human sperm cells treated with detergent to remove their plasma membranes (FIG. 4A), isolated human sperm cell tails treated with detergent (FIG. 4B), or isolated human sperm cell heads treated with detergent (FIG. 4C). 2-fold serial dilutions of sperm cells, sperm cell tails, or sperm cell heads were used to evaluate apparent dissociation constants for different aptamer clones and for a random library. Aptamer specificity was verified by testing against HeLa cells (FIG. 4D). Solid lines in the graphs are fits of the data using the Hill equation.
Figure 4B:
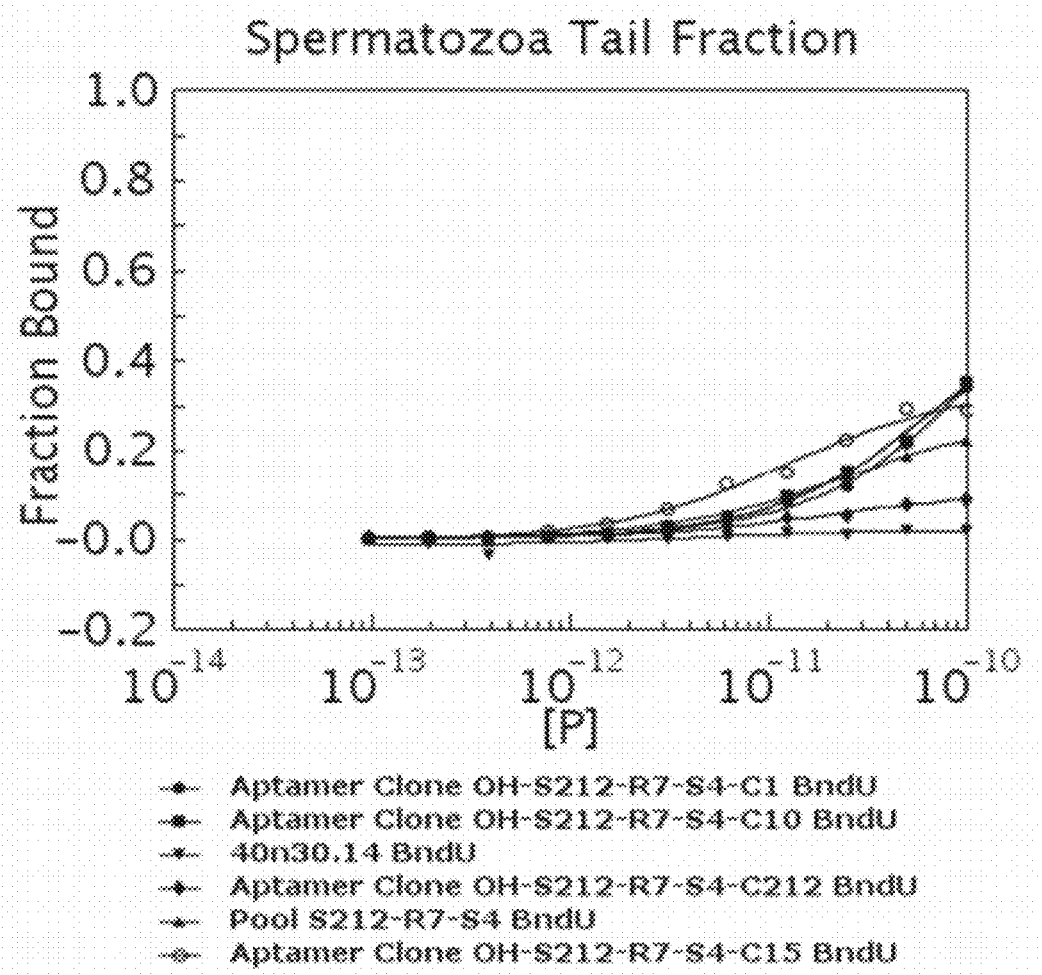
Figure 4C:
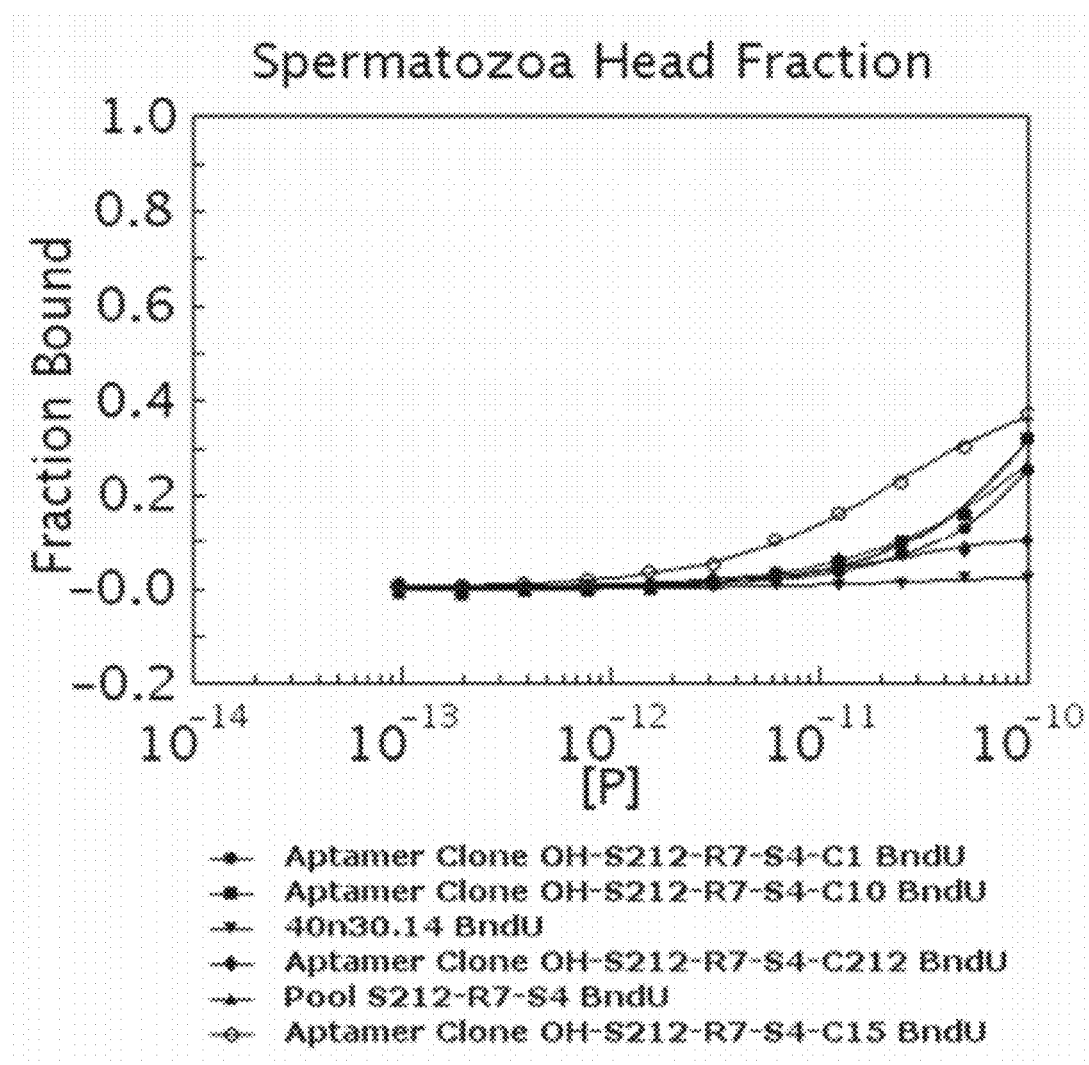
Figure 4D:
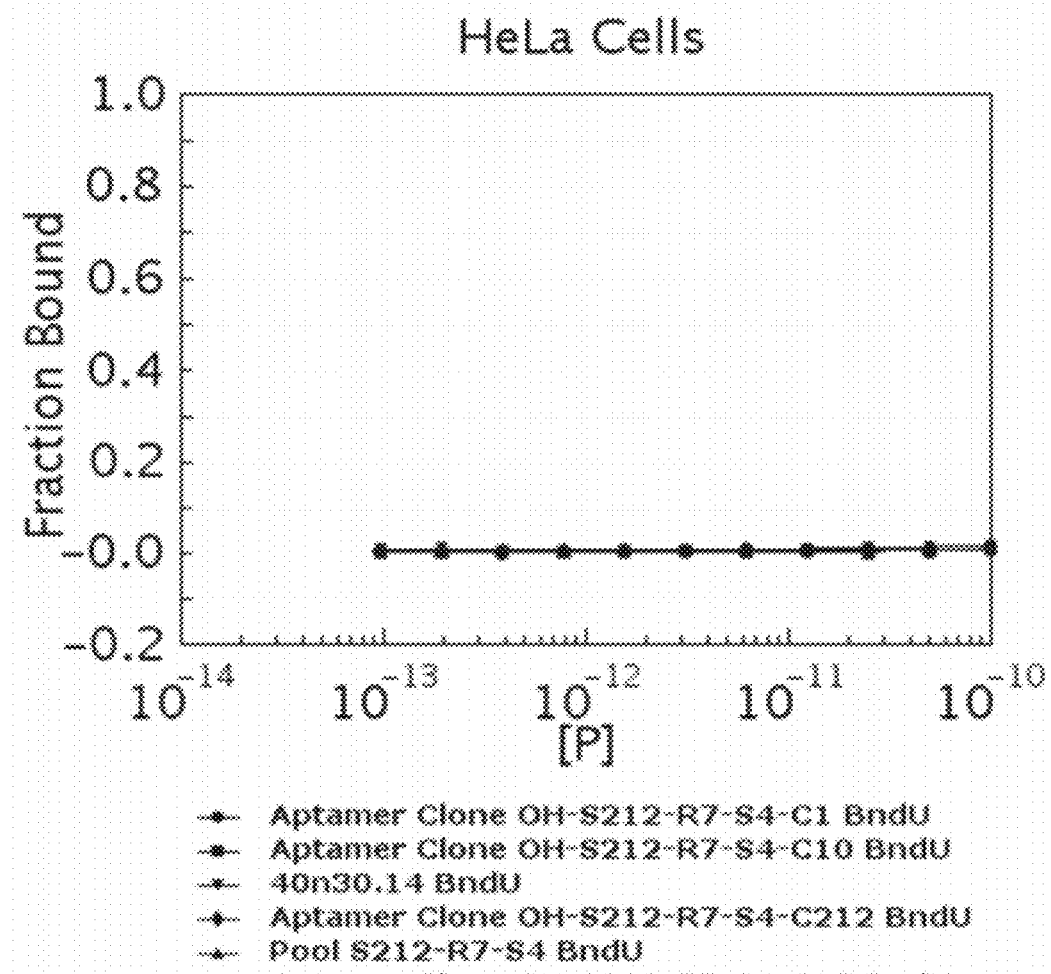

After seven rounds of selection, aptamer pools were cloned and individual aptamer sequences determined. Individual aptamers were generated by primer extension from isolated plasmid DNA, and tested for binding to sperm cells and for binding to HeLa cells, which as noted above, was used as an epithelial cell surrogate. FIGS. 4A and 4B illustrate graphically selective binding to sperm, cells for a number of the aptamers isolated from selection using detergent treated sperm cells.

Sperm Pull Down Assays

Figure 7:
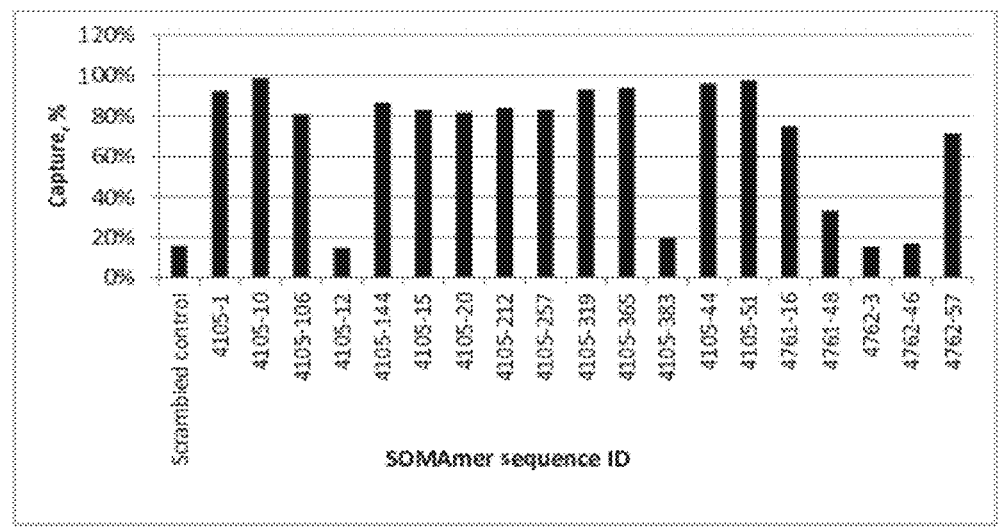
FIG. 7 depicts graphically the isolation of sperm cells from solution using magnetic beads coated with various aptamers as described in Examples 1 and 2.

Selected aptamers were synthesized with a biotin moiety appended to the 5' end, and tested in a sperm cell pull down assay in solution. Briefly, aptamers were immobilized on magnetic streptavidin beads and incubated with sperm in selection buffer containing 100 µM dextran sulfate as a non-specific competitor. The results are depicted in FIG. 7, which illustrates that several of the aptamers tested were able to support capture and pull down of nearly 100% of sperm cells in solution.

Sperm Elution and Capture from Cotton Swabs

Cellular material elution from forensic swabs is typically performed using 1-2% solution of sodium lauryl sulfate (sodium dodecyl sulfate, SDS). SDS is an efficient medium for recovery of cells, typically resulting in 70-80% of cell recovery (Norris et al. (2007) J Forensic Sci, 52(4):800-805), it was anticipated however, that SDS would be incompatible with aptamer binding due to its capacity to denature proteins and disrupt protein-protein interactions. The selection buffer chosen was intended to support efficient aptamer binding, as well as, efficient elution from cottons swabs. A high concentration of sodium chloride and the mild, non-ionic detergent Triton X-100 were included to disrupt hydrogen bond networks and hydrophobic interactions, respectively. The efficiency of elution of sperm from cotton swabs to which semen had been adsorbed was tested using the selection buffers at various concentrations as compared to a solution containing 1% SDS (intended to mimic differential elution buffer). In these experiments, it was determined that Triton X-100 containing selection buffer yielded cell recoveries that compared favorably with the recovery by SDS containing solution. Recoveries ranged from 44% of the SDS control using the selection buffer to 78% of the SDS control using 2-fold concentrated selection buffer. More concentrated selection buffer (4-fold concentrated) yielded no obvious improvement, with 54% recovery relative to the SDS control.

Figure 8:
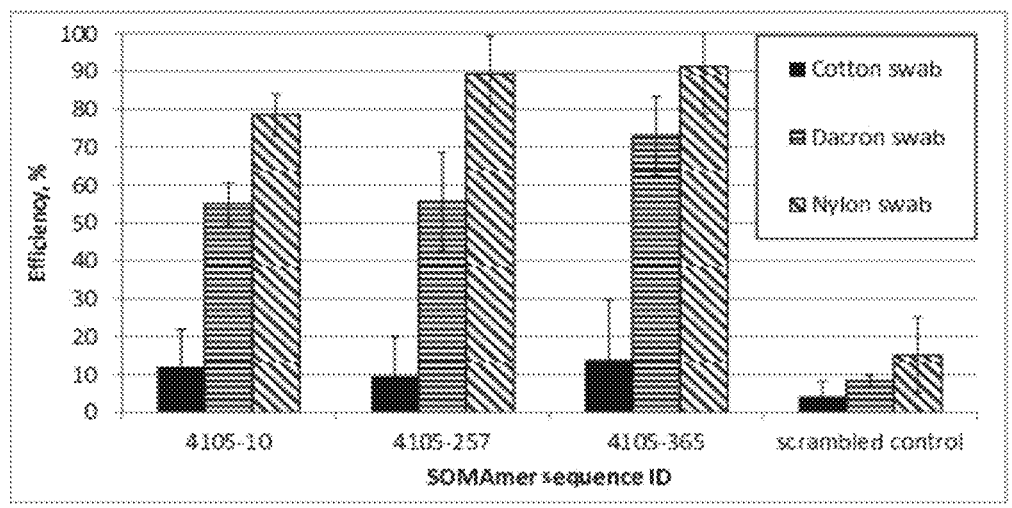
FIG. 8 depicts graphically the efficiency of sperm cell pull down from swab eluted samples using various aptamers.

Having demonstrated the ability to pull down and recover purified sperm cells from solution, the ability to capture sperm cells in samples eluted from swabs. Cotton, Dacron, and nylon swabs were prepared using either purified sperm cells or semen samples. The results are set forth in FIG. 8 which illustrates that the capture and purification of cells eluted from Dacron (polystyrene) or flocked nylon swabs, according to this method is relatively efficient. In particular, cells eluted from flocked nylon swabs can be effectively captured by aptamer coated beads. However, few sperm cells were recovered from cotton swabs.

Swab Elution Condition Screening

Figure 9:
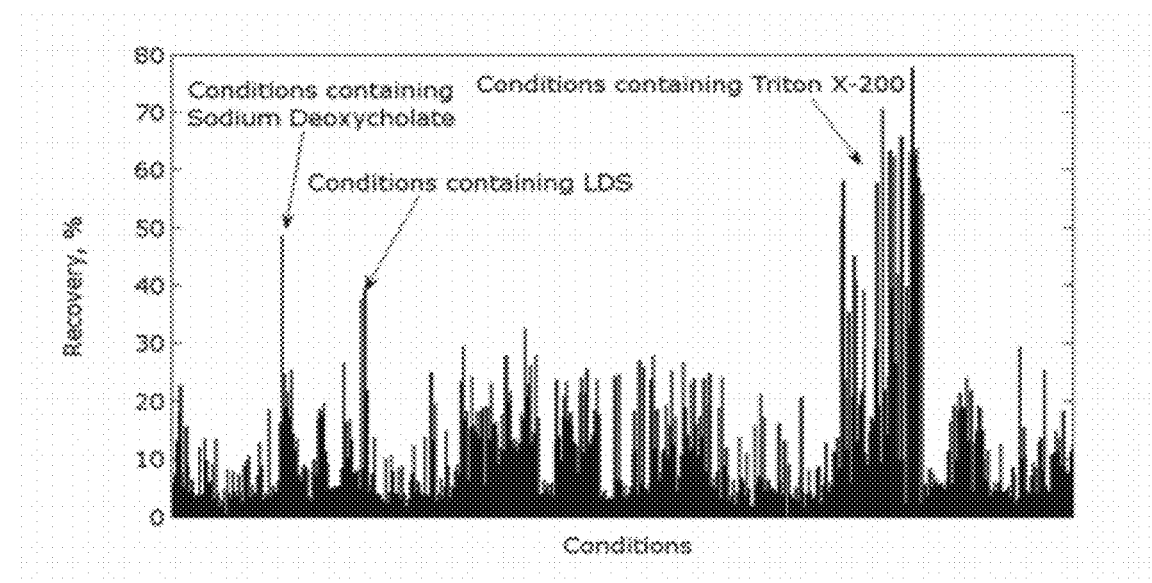
FIG. 9 illustrates sperm recovery from cotton swabs using a variety of buffer conditions for elution and subsequent capture using aptamer coated magnetic beads. Survey of about 500 conditions was performed, each bar in the figure represents a distinct condition.

The inability to efficiently capture sperm cells eluted from cotton swabs has posed a significant problem because most forensic evidence is collected using cotton swabs. Therefore, a number alternative elution buffer conditions were investigated, to find conditions that support both elution and sperm capture from cotton swabs. A large number of conditions (~500) were screened. Specifically, different detergents, salt concentrations, pH's and various additives were screened to determine the critical parameters for both elution and subsequent capture by aptamers. FIG. 9 depicts the global overview of sperm recovery from the swabs using different conditions. It was discovered that majority of conditions tested either did not support effective sperm elution or did not support sperm capture by aptamer-coated magnetic beads. Relatively few conditions were found that supported reasonably efficient sperm elution and capture. These conditions included those that contained anionic detergents Triton X-200, sodium deoxycholate or lithium dodecyl sulfate (LDS) (see FIG. 9). FIG. 10 presents a more detailed analysis of sperm cell elution from cotton swabs in buffers containing various detergents. For presentation clarity, only one particular buffer condition (40 mM Hepes pH 7, 350 mM NaCl) was chosen to represent the trends in the data. Nearly) 80% elution efficiency is achieved in SDS containing buffer, which is currently considered a 'gold' standard. Overall, the best elution efficiencies of sperm cells are achieved when swabs are treated with buffer containing anionic detergents. Lower efficiencies are obtained using zwitterionic and non-ionic detergents, as demonstrated previously (Norris et al. (2007) J Forensic Sci, 52(4):800-805).

Figures 10A, 10B, 10C:
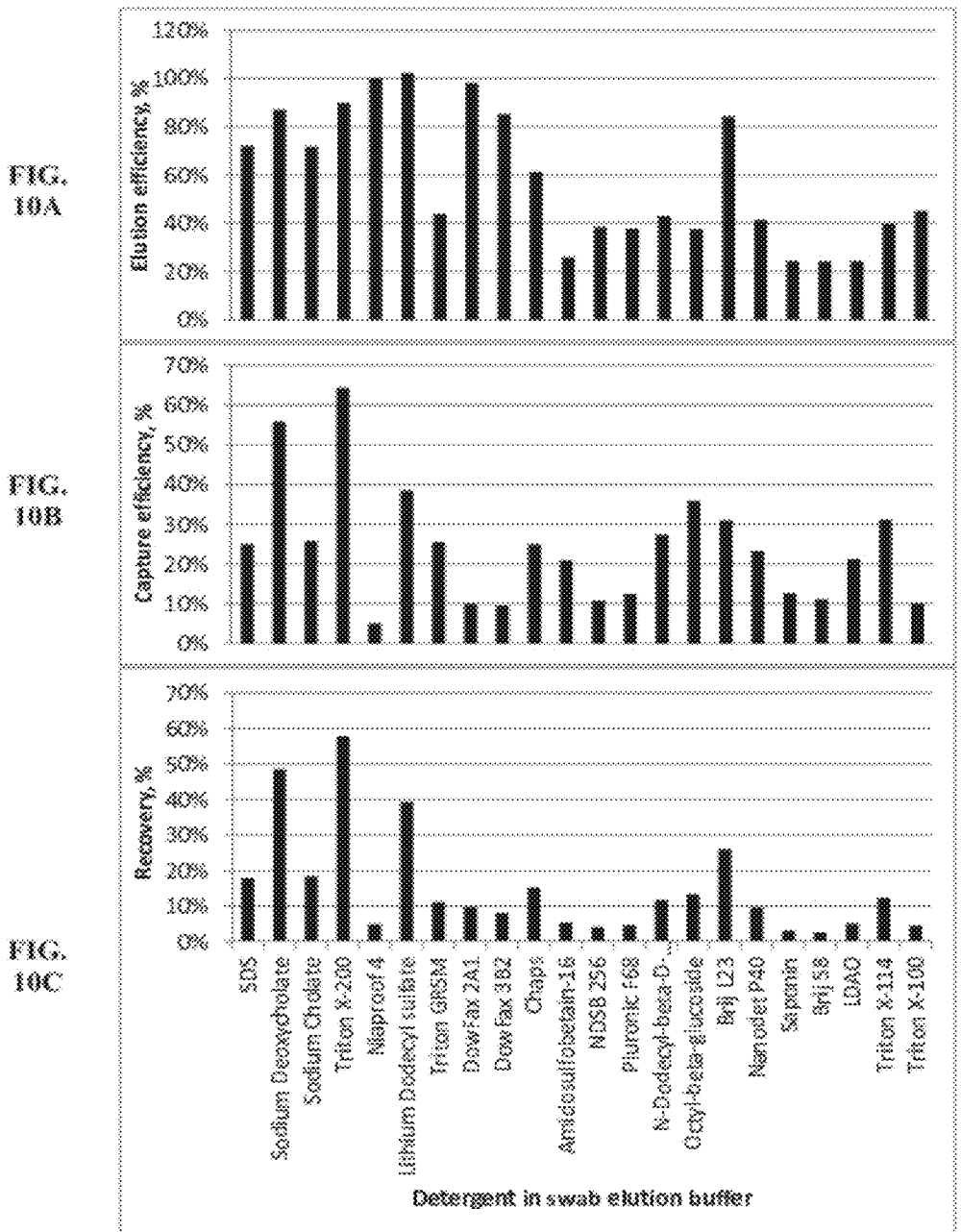
FIGS. 10A-10C depict elution efficiency (FIG. 10A), capture efficiency by aptamers (FIG. 10B) and overall recovery efficiency of sperm cells (FIG. 10C) from cotton swabs using buffers containing different detergents. All detergents were at 1% w/v in 40 mM Hepes pH 7.5, 350 mM NaCl and 0.5 mM EDTA, with the exception of sodium deoxycholate and Triton X-100, which were at 0.1%, and octyl-beta-glucoside, which was at 1 mM concentration.

With reference to FIG. 10B, it can be seen that sperm cells can be effectively captured in buffers containing 0.1% sodium deoxycholate and 1% Triton X-200 detergents, with somewhat lower, but still elevated, efficiency achieved in buffer containing 1% lithium dodecyl sulfate. This is a surprising observation in that these are relatively harsh anionic detergents that would not be expected to support specific aptamer binding to native epitopes.

Sperm Purification from Samples Eluted from Mock Forensic Swabs

The ability to purify sperm cells from mock forensic swabs, prepared by inoculating cotton swabs with a mixture of HeLa cells and semen was evaluated. As noted above, HeLa cells, derived from a human cervical cancer cell line, serve as a surrogate for human vaginal epithelia. The initial experiments were aimed at determining which detergents support sperm cell purification from these mock forensic swabs. Swabs bearing a 3-fold excess of HeLa cells over sperm cells were eluted in buffer containing either Triton X-200, deoxycholate or lithium dodecyl sulfate detergents. After elution, magnetic beads coated with aptamers (see above) were added to the eluate and solution incubated for 15 minutes at room temperature with gentle mixing. Beads were washed once with buffer, and captured cells were lysed. DNA was purified from the lysate using the commercially available DNA IQ kit. Y and X chromosome amounts were quantified using commercially available Quantifiler kits (Quantifiler™ Human DNA Quantification Kit and Quantifiler™ Y Human Male DNA Quantification Kit, Applied Biosystems). Table 1 sets forth Ct values, DNA concentration and relative ratio of Y to X chromosome in purified DNA after the assay.

As shown in Table 1, sperm capture and purification is particularly efficient in the buffer containing Triton X-200 detergent. The ratio of Y DNA to X DNA in purified samples using the Triton X-200 containing elution buffer is nearly 100%, indicating near-complete sperm purification (for comparison, DNA isolated from sperm cells was analyzed using the same qPCR kits). Sodium deoxycholate and LDS based buffers were less effective, with some apparent carryover of HeLa cell DNA. Note that overall sperm capture in solution containing Triton X-200 detergent is also considerably more efficient than in other detergents (column 3, compare row 4 with rows 3, 5 and 6), suggesting that this detergent is highly resistant to background interference from eluted HeLa cells or their debris. It has been determined that 10-fold HeLa cell excess is tolerated by the assay (results not shown).

Figure 11A:
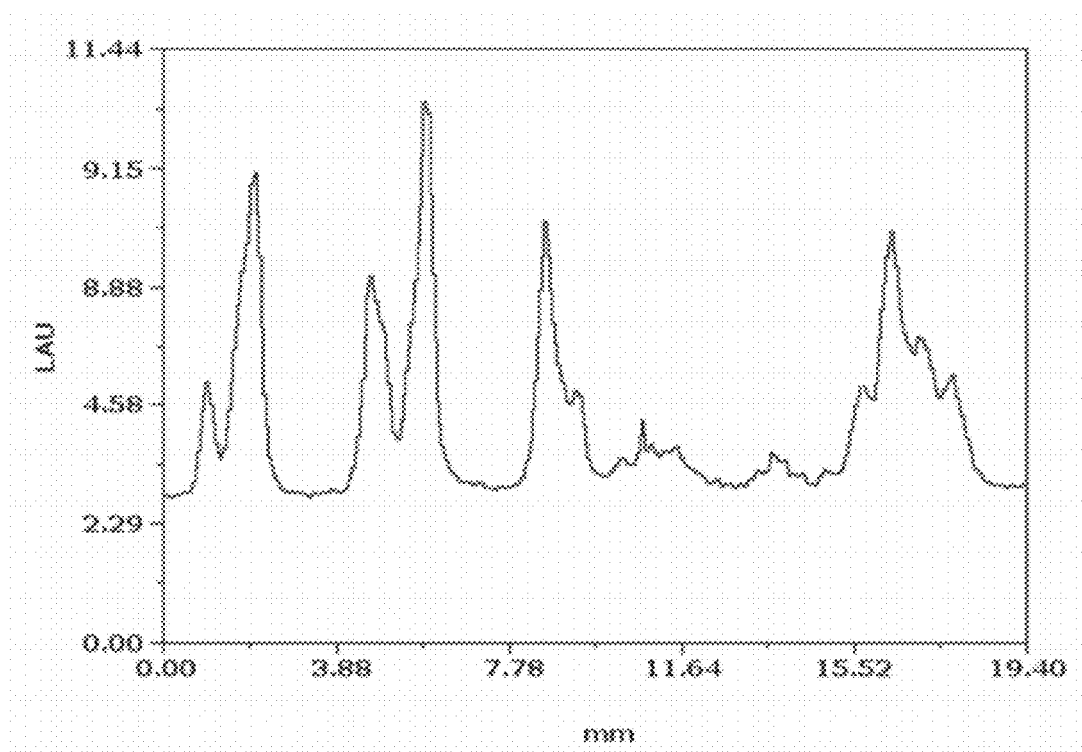
FIGS. 11A-11D depict STR profiles of genomic DNA amplified using GammaSTR kit.
Figure 11B:
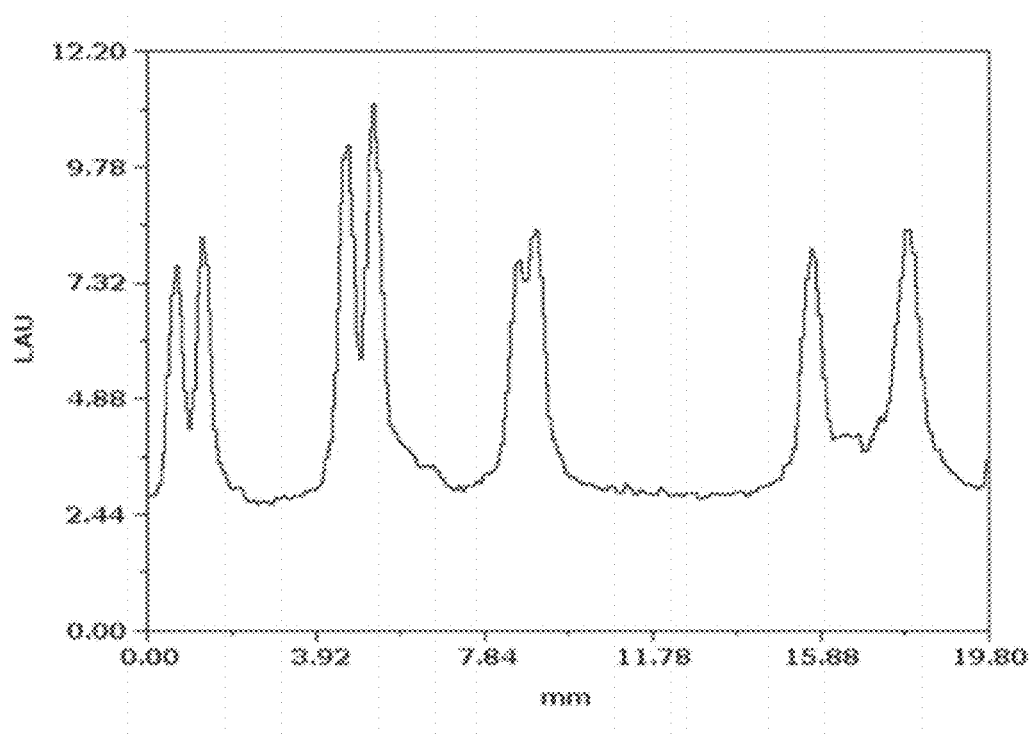
Figure 11C:
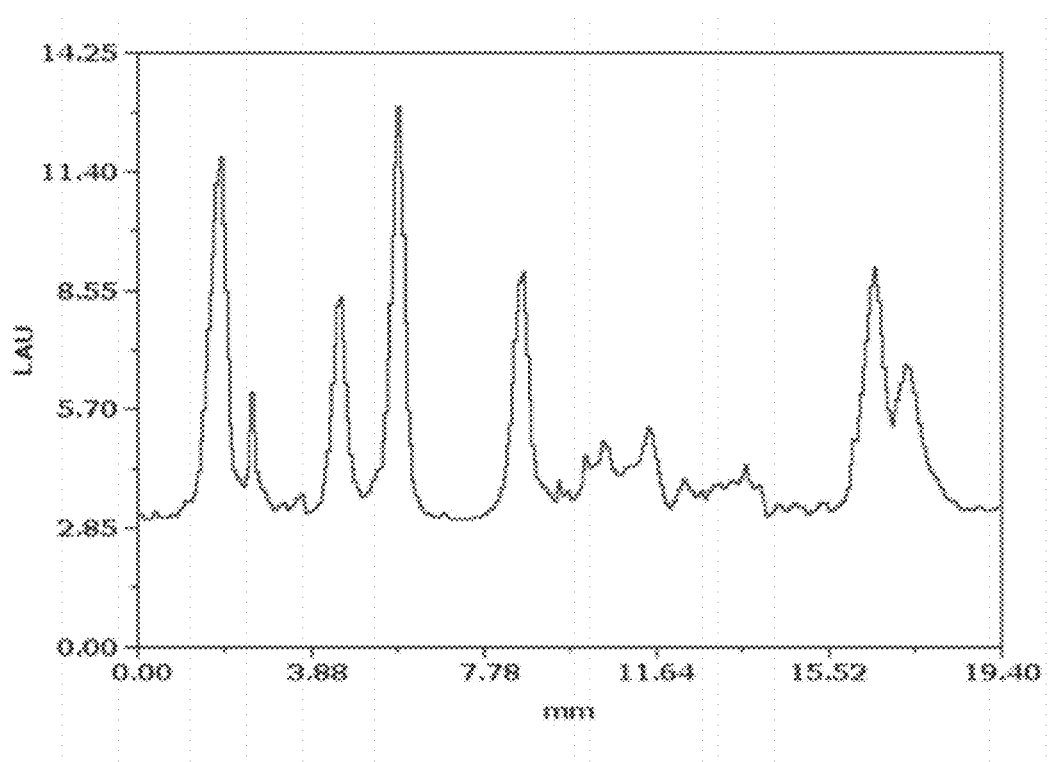
Figure 11D:
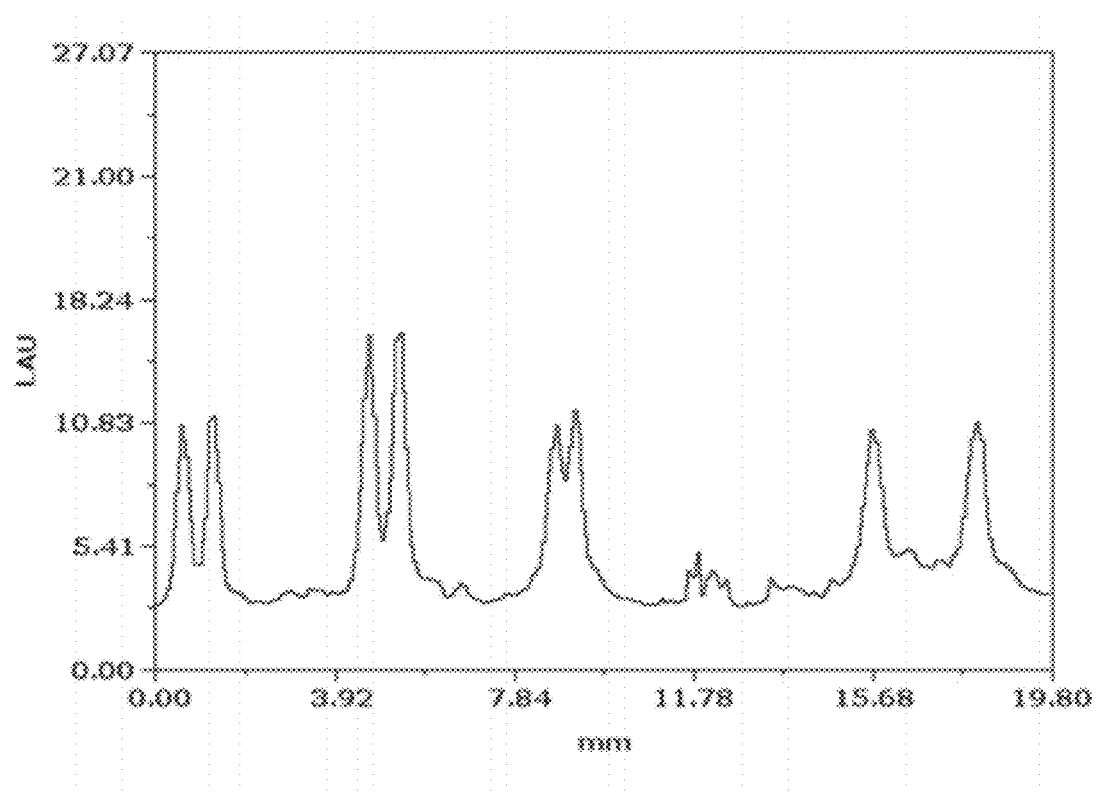
Figure 12A:
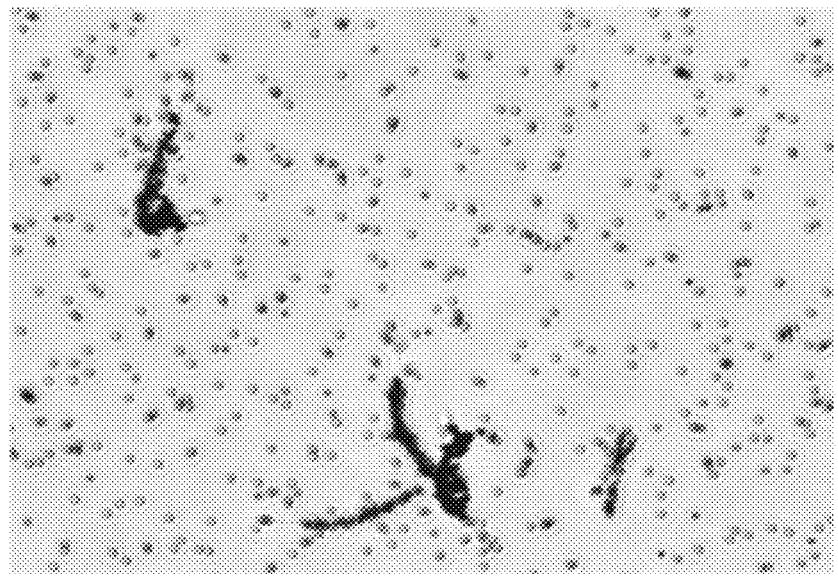
FIGS. 12A-12D depict optical micrographs of aptamer coated magnetic beads bound to sperm cells. Preferential localization of beads coated with different aptamers can be observed.
Figure 12B:
Figure 12C:
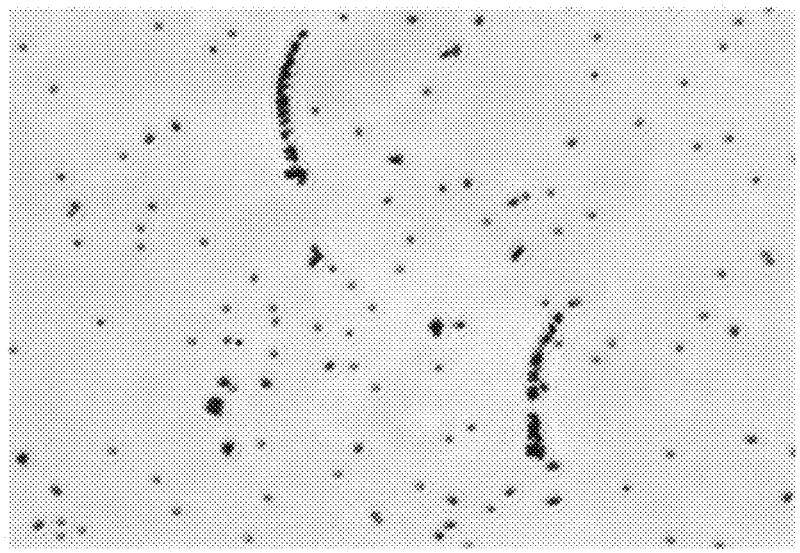
Figure 12D:
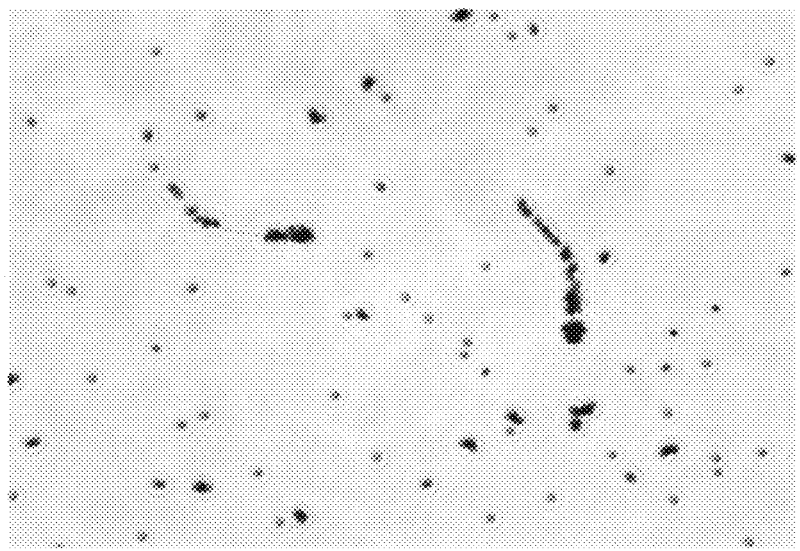

To demonstrate that separation of allelic profiles of respective male and female contributions from forensic samples can be achieved, STR profiles of DNA recovered and purified from mock forensic samples containing a 5-fold excess of HeLa cells (similar results can be obtained from swabs containing 10-fold HeLa cell excess as well) was generated. Four loci were amplified and characterized: D16S539, D7S820, D13S317 and D5S818. Short terminal repeat (STR) profiles generated from amplified DNA fractionated on 6% polyacrylamide-urea gels are shown in FIG. 11. In FIG. 11A, DNA from the eluted sample was profiled without further purification on aptamer-substituted magnetic beads. The DNA profile is mostly representative of female (HeLa) cells (compare to FIG. 11C, HeLa cell control) as one might expect for swabs prepared with an excess of HeLa cells. In FIG. 12B, eluates were subject to sperm capture and purification using aptamer coated magnetic beads prior to DNA purification and profiling. The resulting profile closely matches the profile of the semen DNA control (compare FIG. 11B with FIG. 11D). Thus, it was conclude that purification on aptamer-coated magnetic beads was sufficient to generate a clean sperm STR profile from a mixture of HeLa cells and sperm adsorbed to cotton swabs.

EXAMPLES

The following examples are provided for illustrative purposes only and are not intended to limit the scope of the invention as defined in the appended claims.

Materials and Methods

All chemicals were purchased from Sigma Aldrich unless noted otherwise. Sperm cells (research vials, prepared by density gradient centrifugation and subsequent washing) were obtained from California Cryobank. Semen samples were obtained from Lee Biosolutions. Radiolabeled nucleoside triphosphates and deoxynucleoside triphosphates were purchased from Perkin-Elmer. Magnetic streptavidin beads (MyOne C1) were purchased from Invitrogen. KOD DNA polymerase was purchased from EMD Biosciences. Oligonucleotide primers were purchased from Integrated DNA Technologies. Oligonucleotide libraries containing 40N random regions were purchased from Trilink.

Example 1

Generation of High Affinity Aptamers to Sperm Cells

Cell SELEX

Figure 3:
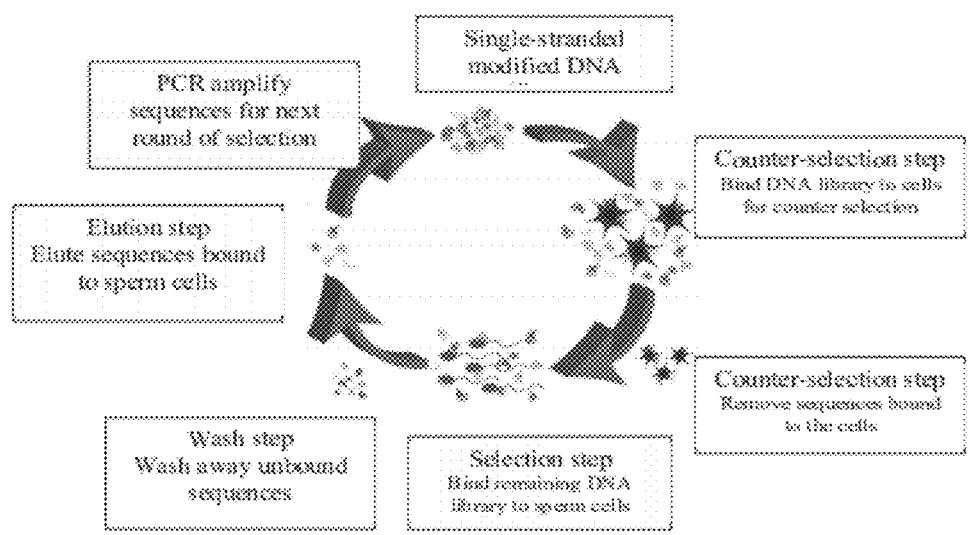
FIG. 3 illustrates an exemplary whole cell SELEX process which includes the step of incorporating a slow off-rate enrichment process.

Aptamers which specifically bind to sperm cells were selected using whole-cell SELEX as illustrated in FIG. 3. An aptamer library consisting of roughly $10^{14}$ molecules composed of a central 40-nucleotide variable region flanked by common primer regions was used. The aptamer library was mixed with sperm cells in the presence of non-specific competitors. After incubation, cells were pelleted by centrifugation, and non-specifically bound aptamers were removed via several wash steps. Bound aptamers were recovered and amplified via the polymerase chain reaction (PCR) to generate a pool of aptamers enriched for their ability to bind to sperm cells. This selection cycle was repeated 8 times. At the end of the round 9, recovered slow off-rate aptamers were cloned and sequenced. Individual slow off-rate aptamers were then generated by primer extension from isolated plasmids, purified, and characterized.

Slow Off-Rate Aptamer Affinity Characterization

Two selections were performed. In the first, aptamers were selected using intact human sperm cells. In the second, selection was done using human sperm cells and bull sperm heads. Human and bull cells were alternated during rounds of selection, with the goal of selecting aptamers targeted to conserved proteins of the sperm head. HeLa cells served as a surrogate for human female epithelial cells.

Selected aptamers were characterized for their affinity and specificity to human sperm cells. Affinity measurements were performed with radiolabeled aptamers. After equilibration of labeled aptamers and sperm cells, cell-aptamer complexes were captured on the nitrocellulose filter and the retained radioactivity was measured. A two-fold serial dilution of sperm cells was used to evaluate apparent dissociation constant for different aptamer clones. Aptamer specificity was verified using HeLa cells as a target. The results are set forth in FIGS. 4A-4D.

Aptamer-Dependent Magnetic Bead Binding to Sperm Cells

Figure 5A:
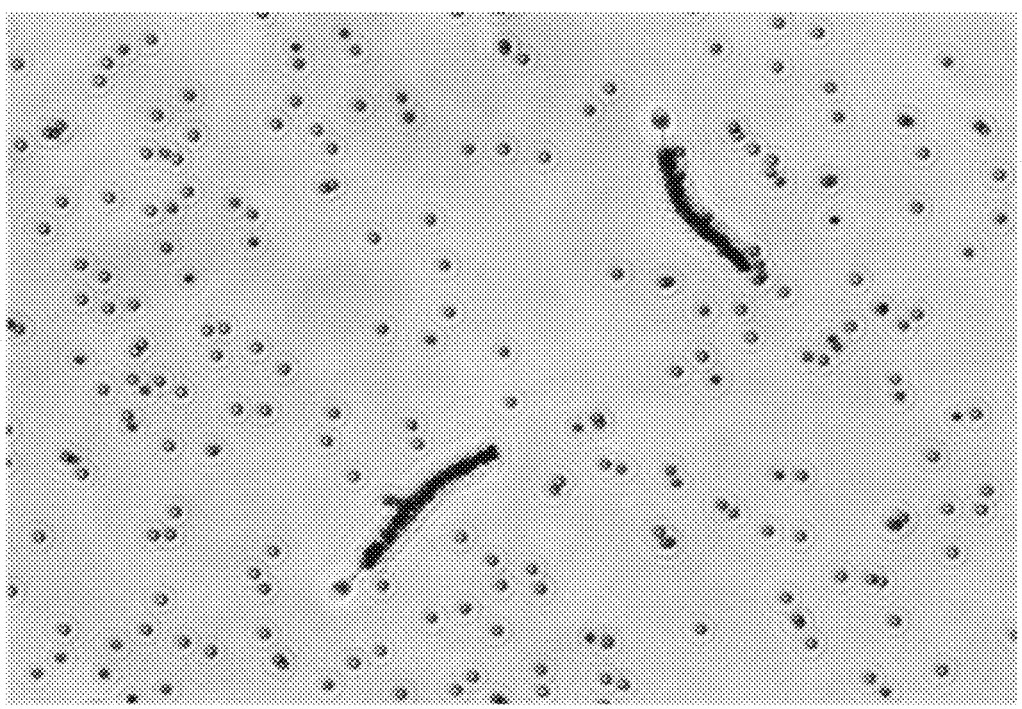
FIGS. 5A-5C depict light micrographs demonstrating slow off-rate aptamer-dependent magnetic bead binding to sperm cells.
Figure 5B:
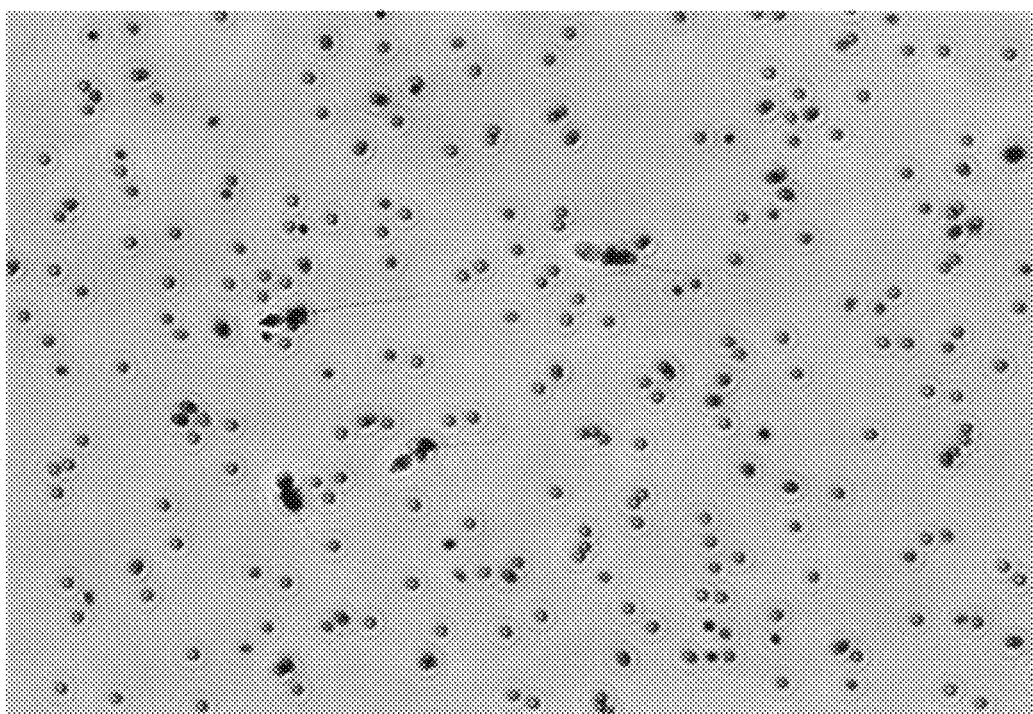
Figure 5C:
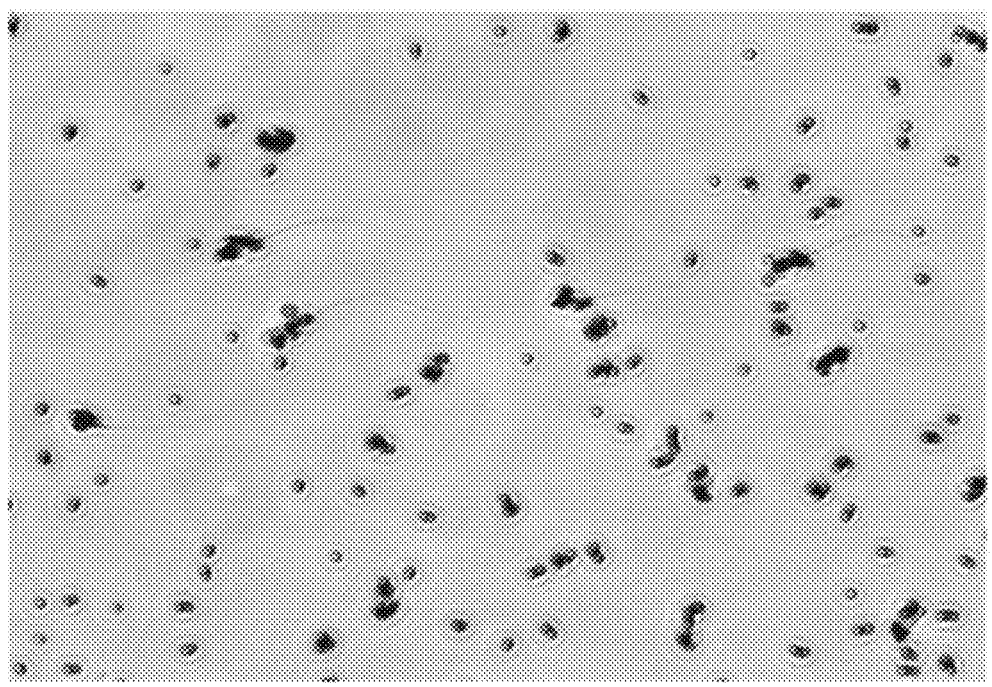

Magnetic beads (1 mm MyOne streptavidin coated beads) were coated with biotinylated aptamers and incubated with human sperm cells in buffer used for selection. Different aptamers show preferential binding to sperm tails (FIG. 5A), midsections (FIG. 5B) or sperm heads (FIG. 5C).

Aptamer-Dependent Sperm Cell Purification

Figure 6:
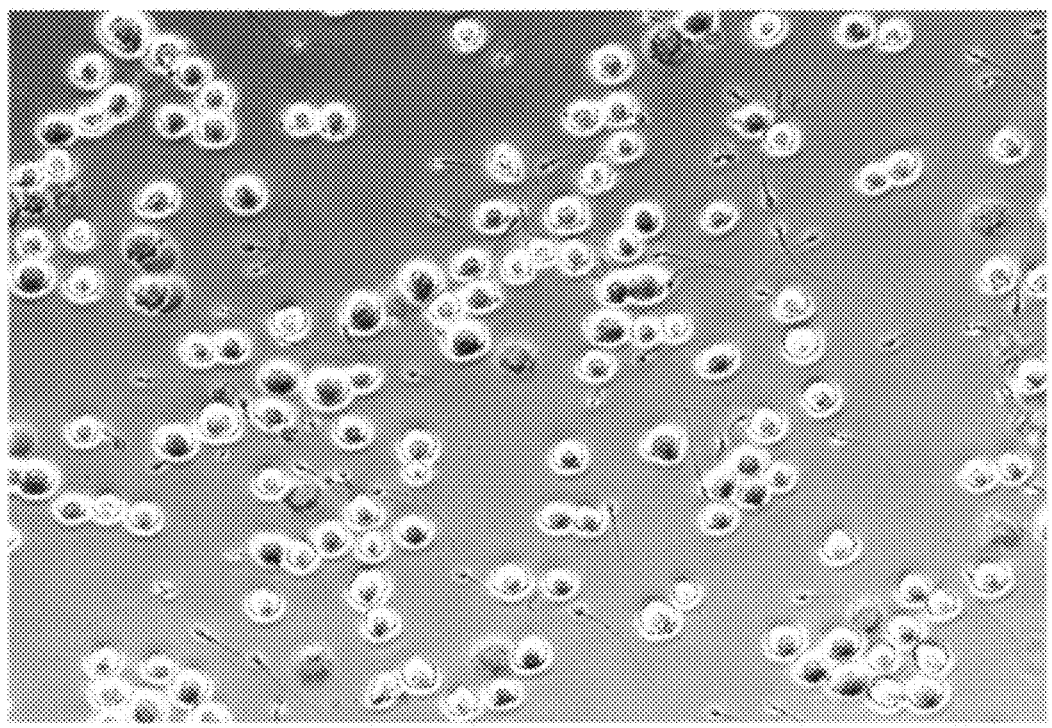
FIG. 6 depicts the results of the purification of aptamer-dependent sperm cells as described in Example 1.

To purify biotinylated aptamers were immobilized on a streptavidin coated micro-titer well. A mixture of HeLa cells (a surrogate for human female epithelial cells) and sperm cells were allowed to bind to the surface. HeLa cells were washed away, while sperm cells were retained on the surface of the microtiter well (FIG. 6).

Example 2

Method for Generating High Affinity Aptamers to Detergent Treated Sperm Cells

Selection Protocol

Selection buffer consisted of 40 mM Hepes pH 7.5, 350 mM NaCl, 1 mM EDTA, 0.5 mM EGTA, and 0.1% Triton X100 detergent. Libraries containing modified deoxyuridine base were prepared by enzymatic primer extension reactions using a biotinylated anti-sense oligonucleotide library consisting of 40 random deoxynucleotides flanked by constant regions (ggcagtccgtccgtc (SEQ ID NO: 1) at the 5' end; gccagaagcagaaggacg (SEQ ID NO: 2) at the 3' end, containing two biotin molecules at 3' end). Antisense libraries were immobilized on the streptavidin coated agarose beads, and a 5' primer was added with a reaction mixture containing dA, dC and dG as well as modified dU deoxynucleoside triphosphates (0.8 mM each) and KOD DNA polymerase (0.1 unit/µL) in appropriate buffer. The reaction mix was incubated for two hours at 68° C. Extended DNA molecules were eluted with 20 mM NaOH, and solution neutralized to neutral pH with HCl. The resulting aptamer libraries were concentrated on YM10 centrifugal ultrafiltration units, quantified, and analyzed by gel electrophoresis.

Preparation of Sperm Cells for Selection Using Detergent

Sperm cells were prepared for selection by washing them three times with selection buffer supplemented with Triton X100 detergent and NaCl to final concentrations of 1% and 600 mM, respectively, followed by suspension in selection buffer. Libraries containing approximately $1.5 \times 10^{15}$ molecules in selection buffer were heated to 95° C., then slowly cooled to 37° C. Aptamer libraries were then combined with an equal volume of a competitor solution composed of 2 mg/mL herring sperm DNA, 2 mg/mL yeast tRNA, 200 µM dextran sulfate, 2 µM prothrombin, 2 µM casein, and 2 mg/mL human serum albumin in selection buffer. Note that the high-salt conditions and high concentrations of competitor were found to be important to diminish non-specific binding of aptamer library DNA to sperm cells. $10^7$ HeLa cells were added and the mixtures were incubated for ten minutes. HeLa cells and debris were pelleted by centrifugation, and remaining library DNA was recovered with the supernatant. Sperm cells ($10^7$) were then added to the retained depleted library. Cells were incubated with library DNA for 1 hour. Sperm cells were washed with selection buffer 8 times, washes were performed by pelleting the cells by centrifuging at 6000×g for 5 minutes and removing supernatant. Bound aptamers were eluted from sperm cells by addition of a solution consisting of 40 mM Hepes (pH 7.5), 0.025% SDS, 5 mM EDTA, and 50 mg/mL proteinase K, incubation at 55° C. for 15 minutes, and removal of sperm cells by centrifugation. Eluted aptamer DNA was purified by hybridization to magnetic streptavidin beads substituted with biotinylated 3' primer. Beads were washed and aptamer DNA was recovered by elution with 20 mM NaOH. Eluted aptamer solutions were neutralized and PCR-amplified using 5' and biotinylated 3' primers. Modified aptamer DNA pools prepared as follows: amplified DNA was captured on to magnetic streptavidin beads, and the non-template strand of DNA stripped from the immobilized anti-sense DNA with 20 mM NaOH, generating immobilized template DNA. A 5' DNA primer, KOD DNA polymerase, and deoxynucleoside triphosphates (dA, dC, dG and modified dU each at 0.8 mM) were then added. The mixture was incubated at 68° C. for 1 hour with shaking. The extended products were recovered by elution with 20 mM NaOH and neutralized using HCl. The products were evaluated by gel electrophoresis. Subsequent rounds of selection were performed in a similar fashion, using amplified aptamer pools from the previous round. Seven rounds of selection were performed. The progress of the selection was monitored at the end of each round via measurement of the rate and extent of reassociation of thermally denatured aptamer pools. These so-called C0t curves reflect the complexity of a DNA population and thus serve as a measure of the selection progress. Rounds 3-7 included incubations for increasing periods of time in a solution of 10 mM dextran sulfate in selection buffer. Incubations in dextran sulfate comprise a "kinetic challenge" intended to remove aptamers with high off-rates. After round 7, eluted aptamers were amplified, cloned and sequenced.

Binding Assays

Aptamers were radiolabeled with $^{32}P$ adenosine triphosphate and T4 polynucleotide kinase via standard methods. Radiolabeled aptamers were separated from free label by gel filtration on small spin columns (ProbeQuant G50). Radiolabeled aptamer preparations (about 10,000 cpm/reaction) were combined with sperm cells in selection buffer supplemented with 1 mg/mL herring sperm DNA, 1 mg/mL tRNA, 100 µM dextran sulfate, 100 µg/mL human serum albumin, and 1 µM casein. Reactions were incubated for 1 hour at 37° C., and filtered through filter plates under vacuum. Plates were washed with 200 µL of selection buffer, dried, and exposed to phosphor screens for several hours. Phosphor screens were imaged using Fuji Bioanalytic scanner, images were analyzed and quantified using Image Gauge v4.0 software (Fujifilm).

Sperm Capture Assays

Sperm capture assays were performed using synthetic aptamers bearing a 5' biotin moiety. Biotinylated aptamers were immobilized on magnetic streptavidin beads (MyOne C1, Invitrogen) according to manufacturer suggested protocols, and washed with selection buffer several times prior to assay. Sperm pull-down assays were performed as follows: purified sperm cells were suspended in selection buffer, aptamer-substituted magnetic beads added to the solution (typically 10-20 µg of beads added) and the solution incubated with mixing for 30 minutes to allow for bead binding to cells. After incubation, magnetic beads were washed with selection buffer once, captured cells were lysed by addition of a lysis buffer consisting of 100 µg/mL of proteinase K and 40 mM DTT in selection buffer and incubation at 55° C. for 1 hour. The DNA amount in the cell lysate was quantified using Picogreen assay (Life Technologies).

Mock forensic swabs were prepared by inoculating cotton swabs with solutions containing HeLa cells and semen (or purified sperm). HeLa cells were used as a surrogate for female vaginal epithelial cells. Swabs were, allowed to dry at room temperature for couple hours and then stored at −20° C. until use. Before assay, swabs were kept at room temperature for about 5-10 minutes. Elution was typically performed with 1 mL of elution buffer in 1.7 mL eppendorf tube. Swabs were eluted for about 10 minutes by occasionally swirling them in solution and then solution recovered by squeezing the swab out on the side of the tube.

Elution Condition Screening

A comparison of elution and capture efficiencies of a large number of buffer conditions (~500), including different detergents, salt concentrations, pH and various buffer additives was performed to determine conditions for effective sperm elution from cotton swabs and capture using aptamer coated magnetic beads. Sperm cell elution and capture was assessed by quantification of DNA released from lysed sperm cells, using fluorescence-based methods (Picogreen, Life Technologies). Standard curves were prepared using an appropriately diluted human genomic DNA standard. Sperm cell capture was performed using magnetic beads coated with a mixture of three lead aptamers. Specifically, the assay was performed as follows: cotton swabs were prepared with a small amount (10 µL) of undiluted human semen. Elution was performed under various conditions in a SlicPrep plate (Promega). A portion of the swab eluate was removed, sperm DNA isolated using DNA IQ kit (Promega) and quantified by Picogreen assay. 100 µL of the swab eluate were transferred from the SlicPrep plate into 96-well plate. 20 µg of aptamer-coated magnetic beads were then added to each well, and the plate was shaken at room temperature for 30 minutes to allow for binding between sperm cells and magnetic beads. Aptamer-coated magnetic beads were washed once with a buffer, then captured cells were lysed and DNA amount in the lysate was quantified by Picogreen assay. Sperm elution efficiency was defined as the ratio of the amount of DNA eluted from the swab to the amount DNA in the 10 µL semen sample.

Capture efficiency was defined as the ratio of amount of DNA in the captured cell eluate to the amount of DNA present in the swab eluate.

Aptamer Binding to Sperm Cells

Aptamer binding localization on the sperm cells was investigated using optical microscopy. Aptamer substituted magnetic beads (1 µg) were mixed with purified sperm cells (10⁴ cells) in 25 µL of the selection buffer. Beads were allowed to bind to cells for 15 min at room temperature. After which, the beads were partitioned on the magnet and washed once with 100 µA of selection buffer. Bead pellet, containing captured cells, was resuspended in 20 µL of selection buffer. 10 µL of resuspended bead/cell mixture was placed in the cell counter chamber and imaged using Nikon Eclipse Ti-S microscope. Imaging was done using bright field mode using 20× Plan Fluor microscope objective, images were captured using a Nikon DS-Fi1 digital camera. FIGS. 12A-12D show bead localization on the sperm cells for different aptamers.

TABLE 1

Sperm purification from mixed swabs eluted in different elution buffers

| Detergent used for swab elution | Y chromosome | | X chromosome | | ratio of Y to X |
|---|---|---|---|---|---|
| | Ct | DNA amount, ng/µL | Ct | DNA amount, ng/µL | |
| Sodium deoxycholate | 31.3 | 0.054 | 30.0 | 0.073 | 74% |
| Triton X-200 | 29.5 | 0.40 | 28.4 | 0.47 | 85% |
| Lithium dodecyl sulfate | 33.0 | 0.007 | 30.9 | 0.024 | 31% |
| Triton X-100 | 30.5 | 0.14 | 26.9 | 2.92 | 5% |
| Sperm DNA control | 27.9 | 2.6 | 26.9 | 3.1 | 83% |
| HeLa DNA control | ND | ND | 27.6 | 0.65 | 0% |

ND—not determined, Ct value is below the kit quantification range

TABLE 2

Illustrative sequences to sperm cells

| ID NO: | SEQUENCE* | SEQ IDNO: |
|---|---|---|
| 4105-10 | ggcagtccgtccgtcZGCCAAGCZCZGCACAGGZZZZZ GCGZGAZCZCZGZGCAGgccagaagcagaaggacg | 3 |
| 4105-10 | ggcagtccgtccgtcZGZGZGZZGZGZGZGZZCZZGZZ CZCZGZCZZGGZGAZGgccagaagcagaaggacg | 4 |
| 4105-365 | ggcagtccgtccgtcAZCGACGCZGZGZGZZZGZCZZ CZZGZZZGZZGZCGZGCgccagaagcagaaggacg | 5 |

*Z is BndU

What is claimed is:

1. A method for purifying or enriching sperm cells in a sample wherein said sample is prepared by elution from a swab by contacting the swab with a buffered anionic detergent solution and wherein the detergent is Triton X-200 or sodium deoxycholate comprising:
   contacting said sample with an aptamer that binds to sperm cells, thereby forming aptamer-sperm cell affinity complexes; and
   partitioning the aptamer-sperm cell affinity complexes from the remainder of the sample.

2. A method for purifying sperm cells in a sample wherein said sample is prepared by elution from a swab by contacting the swab with a buffered anionic detergent solution and wherein the detergent is Triton X-200 or sodium deoxycholate comprising:
   immobilizing an aptamer that has a specific affinity for sperm cells and comprising a tag to a solid support in solution;
   contacting said sample with said aptamer bound solid support; thereby forming aptamer-sperm cell affinity complexes; and
   partitioning the aptamer-sperm cell affinity complexes from the remainder of the sample.

3. The method of claim 1, further comprising introducing a slow off-rate enrichment process prior to partitioning.

4. The method of claim 2, further comprising introducing a slow off-rate enrichment process prior to partitioning.

5. A method for purifying or enriching sperm cells in a sample comprising:
   treating said sample with a buffered anionic detergent wherein said detergent is Triton X-200 or sodium deoxycholate;
   contacting said sample with an aptamer that binds to sperm cells, thereby forming aptamer-sperm cell affinity complexes; and
   partitioning the aptamer-sperm cell affinity complexes from the remainder of the sample.

6. The method of claim 5, further comprising introducing a slow off-rate enrichment process prior to partitioning.

7. A method for purifying sperm cells in a sample comprising:
   treating said sample with a buffered anionic detergent wherein said detergent is Triton X-200 or sodium deoxycholate;
   immobilizing an aptamer that has a specific affinity for sperm cells and comprising a tag to a solid support in solution;
   contacting said sample with said aptamer bound solid support; thereby forming aptamer-sperm cell affinity complexes; and
   partitioning the aptamer-sperm cell affinity complexes from the remainder of the sample.

8. The method of claim 7, further comprising introducing a slow off-rate enrichment process prior to partitioning.

* * * * *

UNITED STATES PATENT AND TRADEMARK OFFICE
CERTIFICATE OF CORRECTION

Page 1 of 1

PATENT NO. : 8,703,416 B2
APPLICATION NO. : 13/525271
DATED : April 22, 2014
INVENTOR(S) : Glenn Sanders et al.

It is certified that error appears in the above-identified patent and that said Letters Patent is hereby corrected as shown below:

On the Title Page, Item (60) "Related U.S. Application Data" should read as follows:

-- (60) Provisional application No. 61/498,224, filed on Jun. 17, 2011. --

Signed and Sealed this
Third Day of February, 2015

Michelle K. Lee
*Deputy Director of the United States Patent and Trademark Office*

SEQUENCE LISTING

<160> NUMBER OF SEQ ID NOS: 5

<210> SEQ ID NO 1
<211> LENGTH: 15
<212> TYPE: DNA
<213> ORGANISM: Artificial Sequence
<220> FEATURE:
<223> OTHER INFORMATION: Primer

<400> SEQUENCE: 1

```
ggcagtccgt ccgtc                                                   15

<210> SEQ ID NO 2
<211> LENGTH: 18
<212> TYPE: DNA
<213> ORGANISM: Artificial Sequence
<220> FEATURE:
<223> OTHER INFORMATION: Primer

<400> SEQUENCE: 2
gccagaagca gaaggacg                                                18

<210> SEQ ID NO 3
<211> LENGTH: 73
<212> TYPE: DNA
<213> ORGANISM: Artificial Sequence
<220> FEATURE:
<223> OTHER INFORMATION: Modifications are Benzyl-deoxyuracil
<220> FEATURE:
<221> NAME/KEY: misc_feature
<222> LOCATION: (1)..(73)
<223> OTHER INFORMATION: n = Benzyl-deoxyuracil

<400> SEQUENCE: 3
ggcagtccgt ccgtcngcca agcncngcac aggnnnnngc gngancncng ngcaggccag    60
aagcagaagg acg                                                     73

<210> SEQ ID NO 4
<211> LENGTH: 72
<212> TYPE: DNA
<213> ORGANISM: Artificial Sequence
<220> FEATURE:
<223> OTHER INFORMATION: Modifications are Benzyl-deoxyuracil
<220> FEATURE:
<221> NAME/KEY: misc_feature
<222> LOCATION: (1)..(72)
<223> OTHER INFORMATION: n = Benzyl-deoxyuracil

<400> SEQUENCE: 4
ggcagtccgt ccgtcngngn gnngngngng nncnngnncn cngncnnggn ganggccaga    60
agcagaagga cg                                                      72

<210> SEQ ID NO 5
<211> LENGTH: 73
<212> TYPE: DNA
<213> ORGANISM: Artificial Sequence
<220> FEATURE:
<223> OTHER INFORMATION: Modifications are Benzyl-deoxyuracil
<220> FEATURE:
<221> NAME/KEY: misc_feature
<222> LOCATION: (1)..(73)
<223> OTHER INFORMATION: n = Benzyl-deoxyuracil

<400> SEQUENCE: 5
ggcagtccgt ccgtcancga cgcgngngng nnngncnncn ngnnngnngn cgngcgccag    60
aagcagaagg acg                                                     73
```